(12) United States Patent
Matos

(10) Patent No.: US 8,583,251 B2
(45) Date of Patent: *Nov. 12, 2013

(54) IMPLANTABLE MEDICAL DEVICE WHICH MAY BE CONTROLLED FROM CENTRAL STATION

(71) Applicant: Jeffrey A. Matos, New Rochelle, NY (US)

(72) Inventor: Jeffrey A. Matos, New Rochelle, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/795,250

(22) Filed: Mar. 12, 2013

(65) Prior Publication Data
US 2013/0226265 A1 Aug. 29, 2013

Related U.S. Application Data

(63) Continuation of application No. 12/154,079, filed on May 19, 2008, now Pat. No. 8,473,065.

(60) Provisional application No. 60/930,525, filed on May 17, 2007.

(51) Int. Cl.
*A61N 1/00* (2006.01)

(52) U.S. Cl.
USPC .......................................................... 607/60

(58) Field of Classification Search
USPC .......................................................... 607/60
See application file for complete search history.

(56) References Cited

U.S. PATENT DOCUMENTS

| | | | |
|---|---|---|---|
| 2001/0031997 A1 | 10/2001 | Lee | 607/59 |
| 2002/0052539 A1* | 5/2002 | Haller et al. | 600/300 |
| 2005/0115561 A1 | 6/2005 | Stahmann et al. | 128/200.24 |
| 2007/0162081 A1 | 7/2007 | Yu et al. | 607/18 |

* cited by examiner

*Primary Examiner* — Robert N Wieland
(74) *Attorney, Agent, or Firm* — Karl F. Milde, Jr.; Eckert Seamans Cherin & Mellott, LLC

(57) ABSTRACT

An implantable medical device (IMD) comprises a transmitting/receiving (T/R) device for transmitting medical data sensed from a patient to, and for receiving control signals from, a medical expert (a human medical professional and/or a computerized expert system) at a remote location; an electronic medical treatment device for treating the patient in response to control signals applied thereto; and a sensor circuit, having a sensor circuit output, for producing sensor circuit output signal(s) representing medical data sensed from the patient. The IMD also includes logic device which analyzes the sensor circuit output signal(s) to detect a medical abnormality and, upon detecting an abnormality, either sends a notification signal representing a medical state of said patient to the medical expert at the remote location or sends a local treatment device control signal to the medical treatment device, or does both.

30 Claims, 20 Drawing Sheets

IMPLANTABLE MEDICAL DEVICE WHICH MAY BE CONTROLLED FROM CENTRAL STATION

CROSS REFERENCE TO RELATED PATENTS AND APPLICATIONS

This application claims priority from Provisional Application No. 60/930,525 filed May 17, 2007, and U.S. patent application Ser. No. 12/154,079, filed May 19, 2008, (now U.S. Pat. No. 8,473,065) from which this is a continuation.

The subject matter of this application is related to that of U.S. patent application Ser. No. 10/460,458, now U.S. Pat. No. 7,277,752, and U.S. patent application Ser. No. 11/502,484 which are incorporated herein by reference.

BACKGROUND OF THE INVENTION

An early generation of implantable cardioverter-defibrillators, "ICDs" had one programmable function: on and off. The modem version of the device has dozens of programmable parameters. In fact, it is now not uncommon for physicians who regularly use such devices to not be fully versed in all of the possible programming complexities of the devices that they implant. Furthermore, the optimal value of some programmable parameters cannot be know at the time of device implantation. Physicians will not uncommonly guess at the values to be programmed for anti-tachycardia pacing, because they may not be able to accurately reproduce the tachycardia that a patient may later have. It is therefore not uncommon for physicians to reprogram such parameters, weeks, months or years later, after the occurrence of the actual event showed that they had not guessed well. Occasionally, the examples are striking. A patient, for example with an ICD and both ventricular tachycardia and atrial fibrillation may get not just one but quite a few inappropriate defibrillator shocks, because of an inappropriately selected programmed rate cutoff, stability parameter, etc. The opposite sort of phenomenon may also occur. For example, a patient with known ventricular tachycardia, "VT", at 200 beats per minute, "bpm", may have the VT detect rate of an ICD programmed to 180, and may later collapse because of an unexpected episode of VT below the rate cutoff.

Occasionally, the malfunctioning of an implanted device can have very serious consequences. The Ventritex V-100 defibrillator at one point had a failure mode which resulted in the sudden death of at least one patient. The "fix" for it, was a programming fix, wherein the downloading of certain instructions prevented the device from being subject to this malfunction.

The explosive growth modem communication systems allows for the possibility of remote supervision and management of implantable device, and addressing of the aforementioned problems. An ICD which may be providing numerous inappropriate shocks over a short time period—either due to device malfunction, lead malfunction or inappropriate programming of a properly functioning system, could be remotely identified and reprogrammed, for example.

A variety of other devices which perform critical functions which remote control could enhance. These include cardiac pumps, insulin pumps, brain stimulating devices and others.

There are certain requirements that must be fulfilled if some of the autonomy of device function is to be impinged on. Remote control over a faulty communication link could create problems instead of solving them, so reliability of communications, careful communication monitoring, redundancy and contingency planning, are all features of a remotely controllable implantable device. Since the communication process uses battery power, judicious power management is also a necessity.

SUMMARY OF THE INVENTION

Hereinbelow: Medical Expert, "ME", refers to either a person (a "medical professional") or an expert computational system.

The inventions disclosed herein concern methods and apparatus for remotely controlling implantable medical devices such as ICDs, pacemakers, drug infusion pumps, brain stimulators etc. In order to conserve battery power, the communication link between the device and a medical expert is designed to function only when needed. Such need is defined by preprogramming certain notification criteria, such that the device initiates communication with a ME only when the assistance of that ME may be needed. Following notification the ME may observe the sensor information that the device observes in making a device management decision. Furthermore, the ME may have access to additional information e.g. historical information within the device memory, historical information about the particular patient from one or more accessible databases, and information about a plurality of patients with the device from still other databases. The ME may have a variety of control-sharing relationships with the implanted device ranging from complete control (with simultaneous complete inhibition of internal control circuits), or a sharing arrangement in which, for example, both the ME and the control circuits of the IMD may be able to influence treatment. Following such an encounter, the ME may modify the device functioning by reprogramming a number of parameters (e.g. notification parameters, a value of one or more parameters which define a threshold for treatment, the actual treatment parameters, battery management, and the nature of the control-sharing arrangement for future episodes involving notification).

DETAILED DESCRIPTION OF THE PREFERRED EMBODIMENTS

Figure 1:
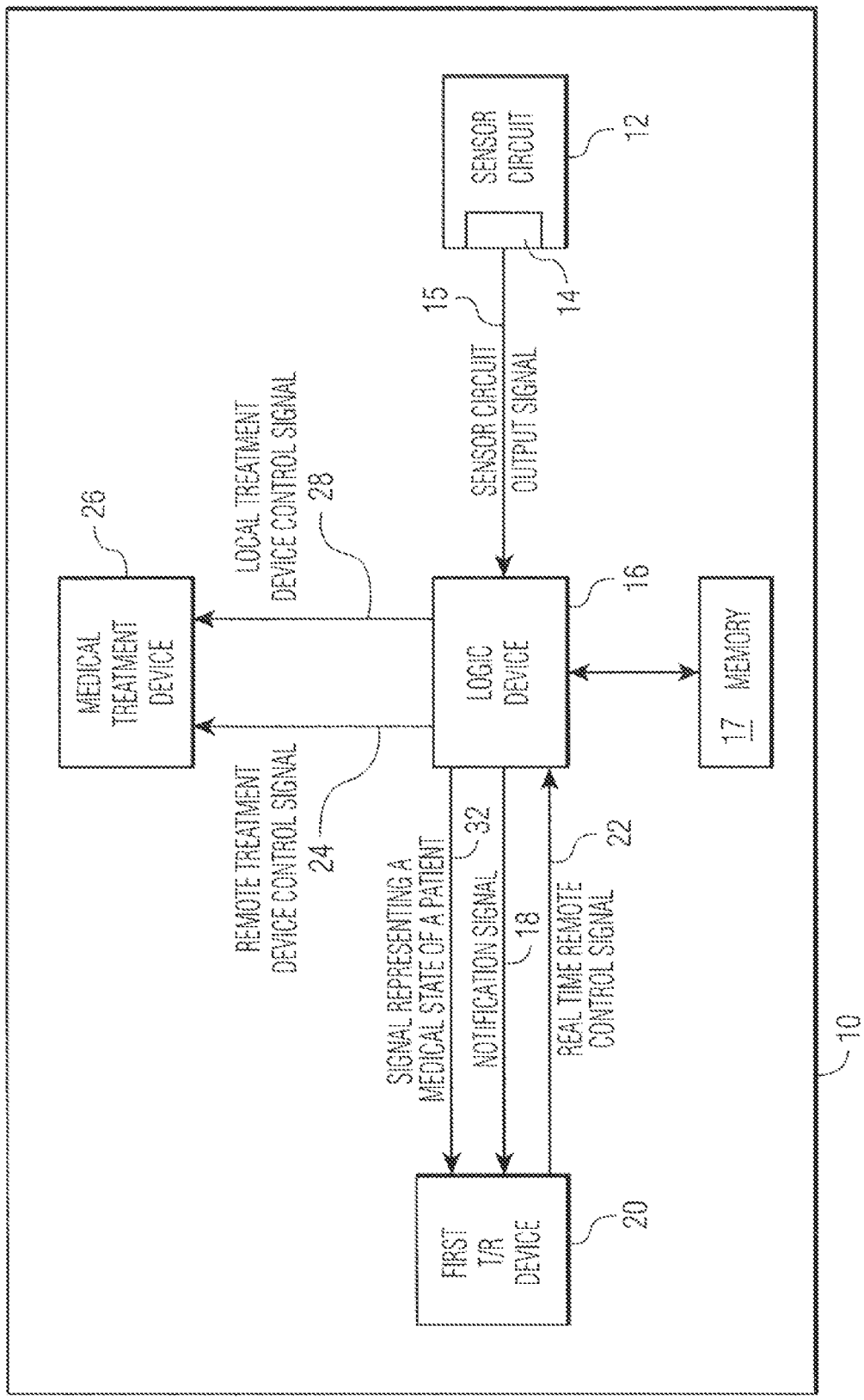
FIG. 1 is a representational block diagram of an implantable medical device ("IMD") which may be remotely controlled.

FIG. 1 shows an implantable medical device 10 which has the capacity to notify a remotely located medical expert. Sensor circuit 12, with output 14, outputs sensor circuit output signals 15. The signals contain data regarding the measurement of at least one medical parameter, a parameter which allows the logic device 16 of the IMD to make treatment decisions. 15 may be an analog signal or a digitized one, as is known in the art. Means for amplification, of 15 and other techniques for signal management as are known in the art, may reside within 12. The sensor circuit is coupled to a sensor, as discussed hereinbelow.

Logic device 16 analyzes signals 15 to determine if there is a need for (a) treatment of a medical abnormality, and/or (b) notification of a remotely located medical expert. Scenarios are possible in which:
1) the abnormality which calls for notification is the same as that which call for treatment;
2) the abnormality which calls for notification is less severe than that which requires treatment;
3) the abnormality which calls for notification is more severe than that which requires treatment; and
4) the abnormality which calls for notification is different than that which requires treatment.

By way of example: In the case of 2) and 4) hereinabove, there may be abnormalities which, though not severe enough to always require treatment, might require treatment under certain circumstances which are apparent to an expert person or system. Thus, providing an ICD shock for VT with a rate of over 240 bpm would be likely to represent sound management much of the time, but the desirability of providing an ICD shock for VT at 140 bpm will depend on a variety of circumstances. Some of these may be easily programmed, such as the duration of the event VT. But others may not. If the ICD in the example was connected to multiple sensors, then a complex decision based on the patient's blood pressure, respiratory rate, and even recent medical history and/or response to antitachycardia pacing in the past might all be factors that would be advisably considered in making a shock/no shock decision. In the case of therapy decision making based on multiple sensors, it becomes impossible to simply say that on set of abnormalities is more severe than another, and "different" is the appropriate term. Thus a VT rate of 140 and a blood pressure of 80 systolic may or may not be considered more severe than a situation with VT at 240 and a blood pressure of 90. Clearly, as the number of different types of sensors increases, and treatment decisions must be based on the data from each of them, algorithms will be more difficult to design, and there will be decreasing likelihood that such algorithms can match the decision making ability of a medical expert, "ME" (person or computational system). The value of having the device "seek consultation" with a ME under these circumstances is clear. At times, the blending of information from multiple sensors may be best accomplished using mathematical techniques which are beyond the scope of a routinely implanted device. Ultimately, treatment decisions may be based on complex functions of multiple parameters and time. Note is made of the fact that these functions may not meet all of the formal mathematical criteria of a function, since input data may not be continuous in nature.

By way of yet another example: It may be desirable to notify and ME only in cases of extreme abnormality, and to omit such notification for routine treatments. In such a circumstance, 16 could be operative to treat non-severe abnormalities without notification and to notify a ME for very severe ones. It could be further operative to treat the severe ones unless, having been notified of a severe event, a ME chooses to override the decision of a MP. Thus a single episode of VT at 240 beats per minute might be treated with a shock without notification of an ME, but four episodes of the same VT over 15 minutes might warrant notification.

Device 16 may be a microprocessor, a group of microprocessors or other computational devices as is known in the art. When preset criteria for ME notification have been met, it signals a ME by sending notification signal 18 to first transmitting/receiving device. "first T/R" 20, which is transmitted to the ME. 20 may consist of a single unit which performs both transmitting and receiving functions, or separate units. The transmission methods are discussed hereinbelow. Along with the notification signal, the logic device will send medical data 32 for the ME to evaluate. The data may include (a) actual signals 15, (b) a processed form of 15, e.g. filtered, compressed, etc., (c) a further refined form of 15 [e.g. beat to beat measurements of cardiac RR intervals ], and (d) still further refined forms of data [e.g. the information that 17 of the last 20 beats were at a rate greater than 200].

The ME has a variety of options upon receipt of this information, discussed hereinbelow. If the ME chooses to treat, a real time remote control signal 22 is received by 20 and sent to 16. The logic device is operative to pass two types of control signals to the medical treatment device which it controls, (a) remote signals 24 which initially originate with the ME, and (b) local signals 28 generated by the logic device, based on its analysis of 15.

The logic device may prioritize among ME control signals 22 and its own control signals in a variety of ways:
 a) It may always give priority to ME control signals over its own internally generated control signals. In such a situation, following notification, only the loss of communication with the ME would result in local control.
 b) In the presence of ME control signals, it may not even generate its own control signals;
 c) It may always provide therapy unless there is a specific signal 22 which inhibits its providing therapy;

d) It may provide therapy along with the ME in an "OR" logic fashion, such that either one may cause 16 to cause 26 to treat.

Memory device 17 linked to the logic device. It may be used for the storage of information about patient events, the storage of programs for medical treatment device management and sensor signal processing, the temporary storage of information during a communication exchange with a ME, the storage of write-once-only information, and the storage of rules for notification management.

Figure 2A:
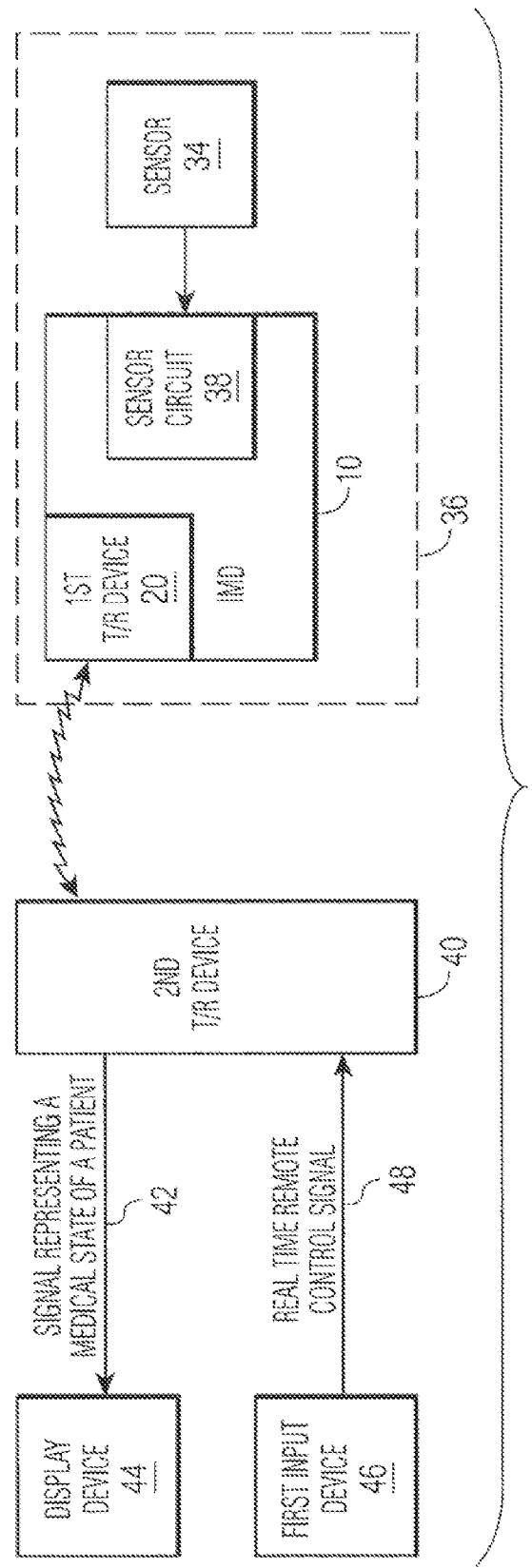
FIG. 2A is a representational block diagram of a system including an IMD, a sensor and a remote station to be operated by a human medical expert.

FIG. 2A shows an embodiment of the invention in which IMD 10 communicates through it first T/R, with a second T/R device 40. 40 provides signals representing a medical state of a patient 42 to be displayed on display device 44. First input device 46 allows an ME to send real time remote control signals to 40, for transmission to 20. 10 and at least one sensor 34 is implanted inside the body of a patient 36. Examples of possible sensors include a pacemaker wire (for sensing cardiac electrograms), a defibrillator lead, a transducer for measuring glucose concentration, a system of conductors for measuring transthoracic impedance, etc. In the embodiment of the invention shown in FIG. 2A, sensor information from 34 is coupled to the sensor circuit 38. IMD 10 transmits the information representing the sensor information (which may be the actual sensor information) via 20 to 40, for display by 44. A human ME may then determine the appropriate treatment, and input it to 46. Signals 48 representing the treatment are transmitted from 40 to 20, thereby to affect the function of 10.

Figure 2B:
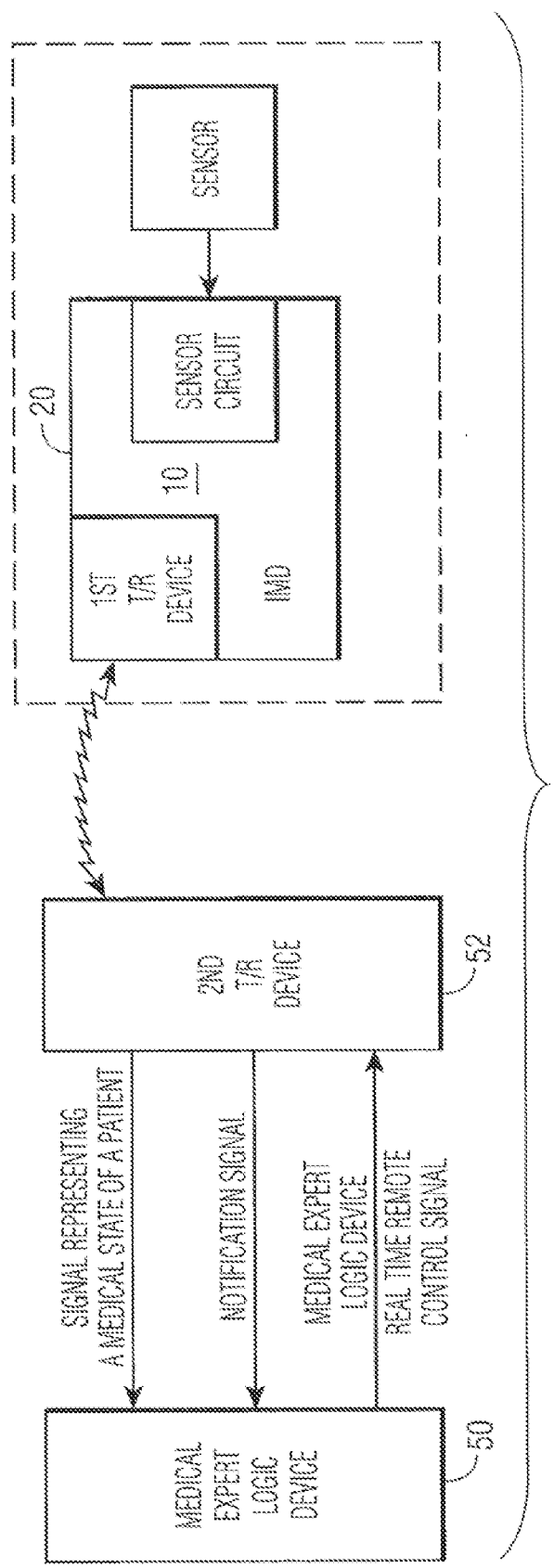
FIG. 2B is a representational block diagram of a system including an IMD, a sensor and a remote station operated by a medical expert computational device.

FIG. 2B shows an embodiment of the invention in which the ME is a medical expert program or group of programs which run on a computational device 50. Each of the signals to and from the first T/R (18, 22 and 32 in FIG. 1) are transmitted between first T/R device 20 and the 2nd TIR of shown herein 52. A device such as 50 would have advantages over the logic device of the IMD including: (a) a much larger memory capacity, such that information may be stored concerning (i) other medical data from this patient; (ii) other medical data from other patients with a similar condition, (iii) performance data about IMD 10; (b) ability to update the database for 52 easily and frequently; and (c) ability to update the algorithms run by 50 easily and frequently.

Figure 2C:
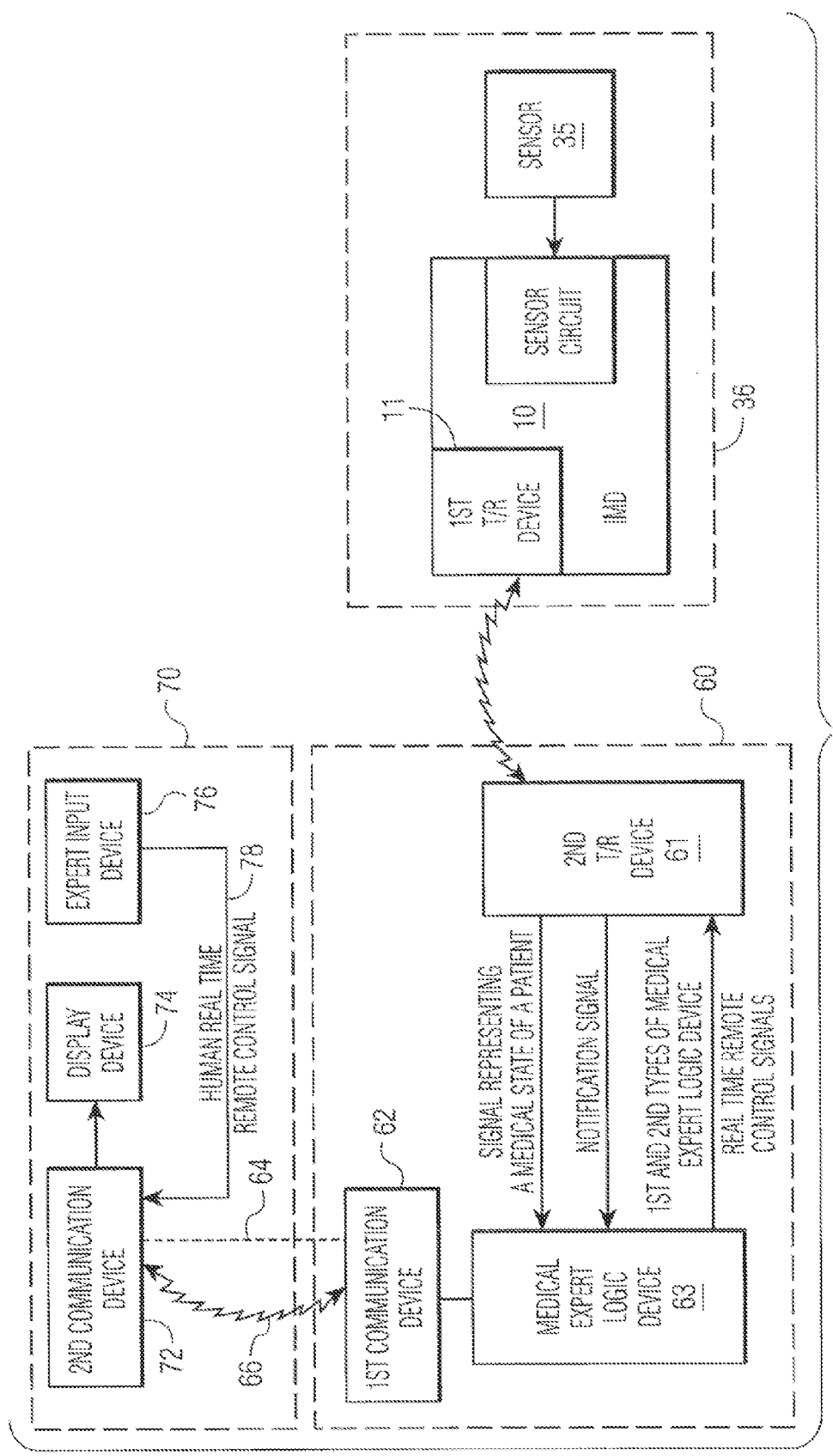
FIG. 2C is a representational block diagram of a system including an IMD, a sensor and a remote station operated by a computational device and a further remote station operated by a human medical expert.

FIG. 2C shows an embodiment of the invention in which IMD 10 in patient 36 communicates with a computer ME 60, which in turn communicates with a human-based ME 70. First communication device 62 in 60 communicates with second communication device 72 in 70; the communication may be either wireless, indicated by signals 66 or wired, indicated by signals 64. The function of 74 is analogous to that of 44 in FIG. 2A, and the function of 76 is analogous to that of 46 in FIG. 2A. The route of the human real time remote control signal is from 76 to 72 to 62 to 63 to 61 to 11 to 10. In an alternate embodiment, the human control signal could be coupled from 62 directly to 61. In yet another embodiment, an RF signal from 72 could be sent directly to 11. The human ME may use each of the following in the process of making a decision: (a) signals (processed and unprocessed) from one or more sensors 35 in patient 36, (b) signals indicating the analysis by the logic device of IMD 10, and (c) signals indicating the analysis by expert logic device 63. There are numerous possible relationships which determine dominance, in terms of control, among each of (i) the human ME, (ii) device 63, and (iii) the IMD logic device. For example:

a) in one embodiment of the invention, human ME signals, if received by the logic device of IMD 10 take precedence over control signals which may have been generated by the IMD logic device and over control signals generated by the analysis of the medical data by 63;

b) in another embodiment, the human may be overruled if both 63 and the IMD logic device disagree with the human;

c) in another embodiment, an "OR" logic prevails, and any one of the IMD logic devices, 63 or the human ME may cause therapy to be delivered;

d) in another embodiment, "AND" logic prevails, and therapy is delivered only if each of the human and 63 and the IMD logic device indicate that treatment is desirable; and e) in another embodiment, any two of the three of the human ME, 63 and the IMD logic device will dominate.

To reliably maintain a system in which the control of an implanted medical device is shared or given over to an outside agent, all possible means to maintain communications integrity must be undertaken. Technique for improving reliability include but are not limited to: (a) redundant communications, (b) the ability to change a route (e.g. wired vs. wireless [though at some point there must be a wireless segment for the implanted device), (c) the ability to change a communications mode (e.g. different means of signal encoding, as is known in the art), (d) the ability to change power output of an RF or other electromagnetic device, (e) the ability to change the sensitivity of a receiver, and (f) the ability to change frequency or channel or telephone number or internet provider.

Figure 3A:
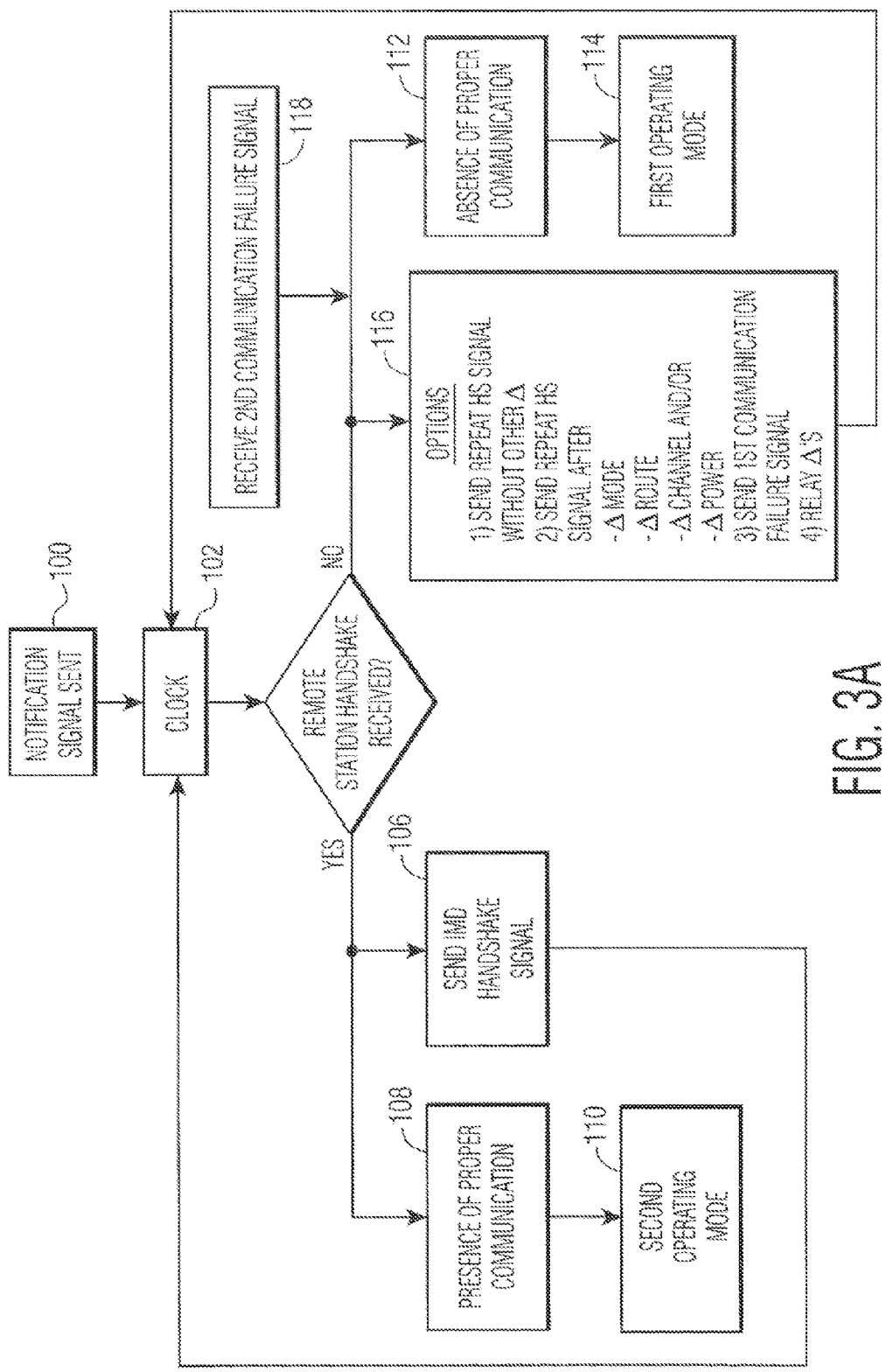
FIG. 3A is a flow diagram of a communication routine for a remotely controllable IMD.
Figure 3B:
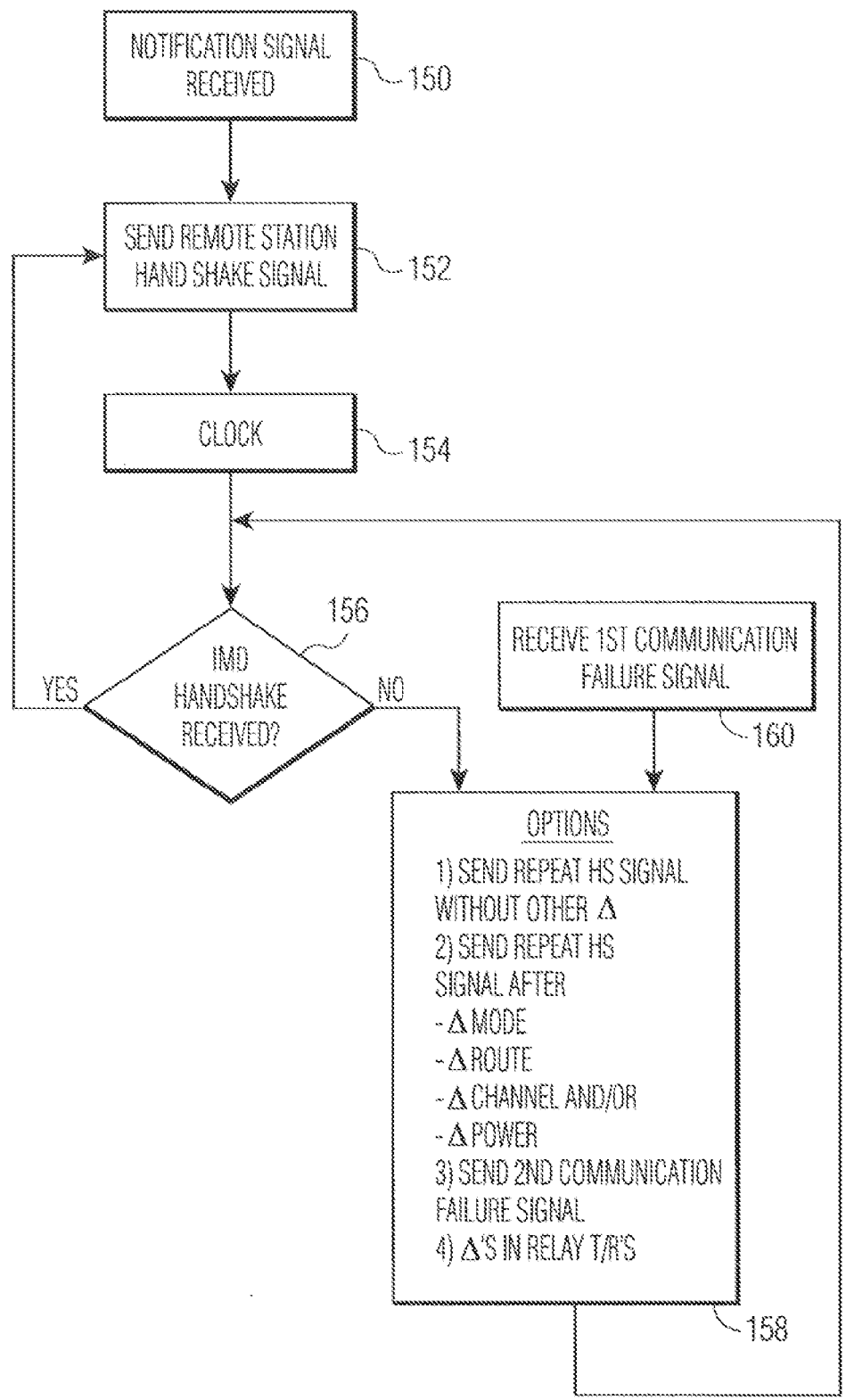
FIG. 3B is a flow diagram of a communication routine for a remote station which communicates with a remotely controllable IMD.

Furthermore, it is important that each of the communicating agents be able to determine whether each segment of the communication path (in each direction) is operative, on a real time basis. For example, if the IMD logic device determines that there has been a break in communication with the ME, it must immediately (a) revert to autonomous operation, and (b) take whatever corrective means it can to restore proper communication. Thus, one embodiment of the invention is operative to cause immediate restoration of device control by the IMD logic device, in the event of a break in communications. To accomplish this, a handshaking routine is operative. FIG. 3A shows the routine at the IMD, and FIG. 3B shows it at the remote station. (Hereinbelow, communication between the IMD and the remote station through one or more relay devices is described. Handshaking routines, known in the art, are possible between (a) each 'adjacent' communicating component in a string of devices, as well as (b) an overall handshake between the remote station and the IMD.

Referring to FIG. 3A, which shows one possible semi-continuous handshaking routine at the IMD, following the transmission of notification signal 100 by the IMD, an interval of time measured by clock 102 is allowed to elapse, waiting for a response, in the form of a remote station handshake signal. If the remote station handshake signal is received in a timely manner, block 104 leads to blocks 106 (resulting in the transmission of an IMD handshake signal by the IMD) and 108, a declaration of the presence of proper communications. The presence of proper communications allows for a second IMD operating mode, in which the IMD is controlled remotely. Block 106 leads to another waiting period determined by 102. In the presence of proper communications, the flow diagram will continuously cycle from 102 to 104 to 106 to 102 . . . . However, if there is an interruption in communications, such that a remote station handshake signal is either not received, or not received in a timely manner, block 104 leads to 112 and the declaration of the absence of proper communications. 112 leads to 114 and a first IMD operating mode. In the first operating mode, the IMD is controlled only by the IMD logic device. In this case, 104 also leads to 116, which lists a menu of options directed at restoring proper communication including: (a) repeat transmission of the remote station handshake signal without any other change; (b) change in either mode, route, power or channel/ frequency, (c) change in the sensitivity, selectivity or other receiver characteristics of the IMD receiver (not listed in the figure), (d) change in the characteristics or choice of an upstream communications relay unit (see below), etc. Each of these choices then leads to another handshake attempt, and another waiting for a response.

It may be possible to determine whether a break in communication occurred in the IMD to remote station direction, or in the reverse direction by the sending and receiving "communication failure" signals. Thus if the IMD receives 118 a second communication failure signal, it implies that the remote station to IMD leg is intact, and it is the IMD to remote station leg that has failed. This helps direct remedial action. Among the items in menu 116 is the sending of a first communication failure signal, to allow the remote station to gain some diagnostic information about the source of the handshake interruption.

FIG. 3B shows one possible version of a handshaking routine at the remote station. Although the determination of a break in communication is far more important at the IMD end (i.e. so that the IMD may resume autonomous function immediately), there are remedial actions that can be accomplished at the remote station end, therefore making the detection of a handshake interruption valuable at that end as well. At block 150, the notification signal is received from the IMD, leading to the transmission of a remote station handshake signal at 152. If after a suitable delay measured by clock 154, there is no received IMD handshake, 156 leads to 158, with a menu of remedial options which are analogous to those in block 156. The intact handshake loop in the diagram is 156, 152, 154, 156 . . . . The broken handshake loop is 156, 152, 156, 158 . . . .

Many other approaches possible handshaking protocols and apparatus will be obvious to those skilled in the art.

Finally (see hereinbelow), downloading a treatment plan or routine for a currently happening ME-IMD session, for storage in the IMD memory, may allow for the completion of a ME set of treatment steps which were interrupted by a break in communications.

Many implanted devices have a low battery drain and a longevity measured in years. If the same battery that supplies a minimal amount of energy for device function (e.g. cardiac pacing, where the current drain may be 10-20 microamps or less) must also supply a transmitter, then unless there is judicious power management, there may be substantial shortening of device battery life. Among the options for accomplishing this are:

a) programming notification criteria so that the function is not over-used;

b) the placement of one or more relay units (see below) in proximity to the IMD/patient, so that transmission from the first T/R involves only short distances;

c) methods of powering down the first T/R, partially, during a transmission, if possible;

d) monitoring battery function so that as the battery ages, the criteria for notification may be made more restrictive;

e) letting the ME know the battery status during a transmission, so that the ME, recognizing an aging battery or batteries, may take action to shorten the current transmission and limit future ones, perhaps by either (i) remotely reprogramming notification criteria, or (ii) remotely programming transmitter power consumption;

f) having a dual power supply arrangement, where one power supply powers only the device T/R (or only the device transmitter), and one power supply powers everything else in the device. An alternate embodiment of this approach would be to the transmitter (or T/R) battery or batteries to be rechargeable.

Figure 4A:
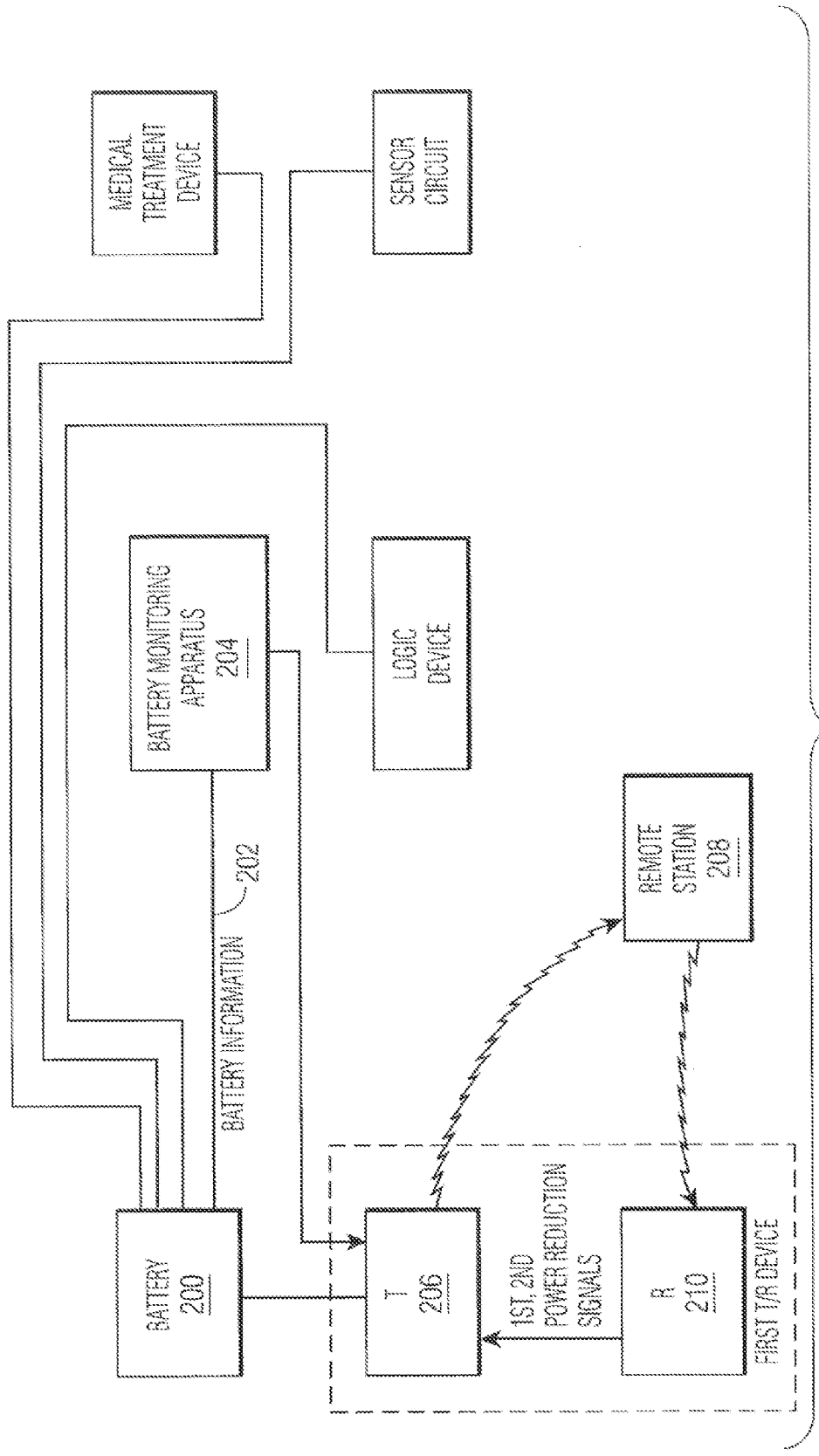
FIG. 4A is a representational block diagram showing remotely controlled power management for a remotely controllable IMD with one battery.

Four exemplary ways of handling battery management are illustrated by the embodiments of the invention shown in FIGS. 4A-4D. Hereinbelow, the word battery may refer to a single cell, two or more cells in series, two or more cells in parallel, and may refer to combinations of these. FIG. 4A contains a single battery 200 which supplies each of the components of the IMD. In addition to supplying the components discussed hereinabove in conjunction with FIG. 1, the battery also supplies battery monitoring apparatus 202 with energy. 202 monitors one or more of battery voltage, cell impedance, battery current drain, the droop in cell voltage with increased demand, and indirect measures of battery function (e.g. the charge time of an ICD). The battery information is supplied to the IMD transmitter 206, for transmission to remote station 208, for assessment by the ME. The ME may use the information for management of real-time power consumption (i.e. reduce transmitter power during the current encounter) by sending a signal to receiver 210, which passes the information contained therein to transmitter 206. Alternatively, the MP may reprogram device performance (e.g. notification criteria), by sending a programming command from 208 to 210 to the logic device (which coupling is not shown in FIG. 4A, but is indicated in FIG. 1.

Figure 4B:
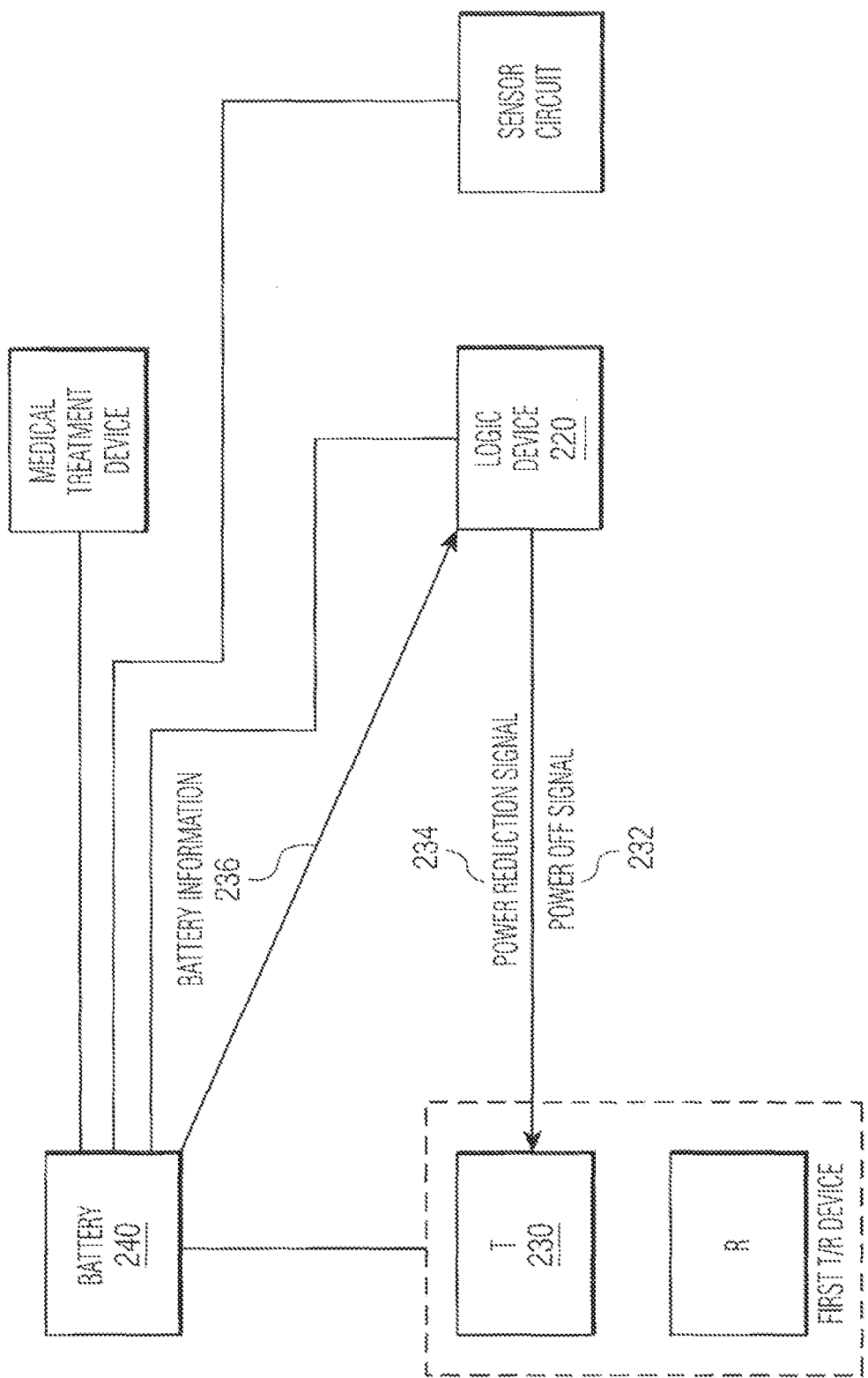
FIG. 4B is a representational block diagram showing locally controlled power management for a remotely controllable IMD with one battery.

FIG. 4B shows a one battery management approach where management is directed within the IMD, i.e. by the IMD logic device. Information 236 about battery 240 (similar to the information discussed hereinabove in conjunction with FIG. 4A) is processed by logic device 220, and may be used maximize the longevity of the battery, as discussed hereinabove. Besides power reduction signals 234 which reduce transmitter 230 power by a variety of possible values, a signal 232 may be sent to power 230 off. As indicated, 220 may also reprogram itself to accomplish such goals as altered notification criterion.

It is possible to combine the attributes of the power conservation approach shown in each of FIGS. 4A and 4B.

Figure 4C:
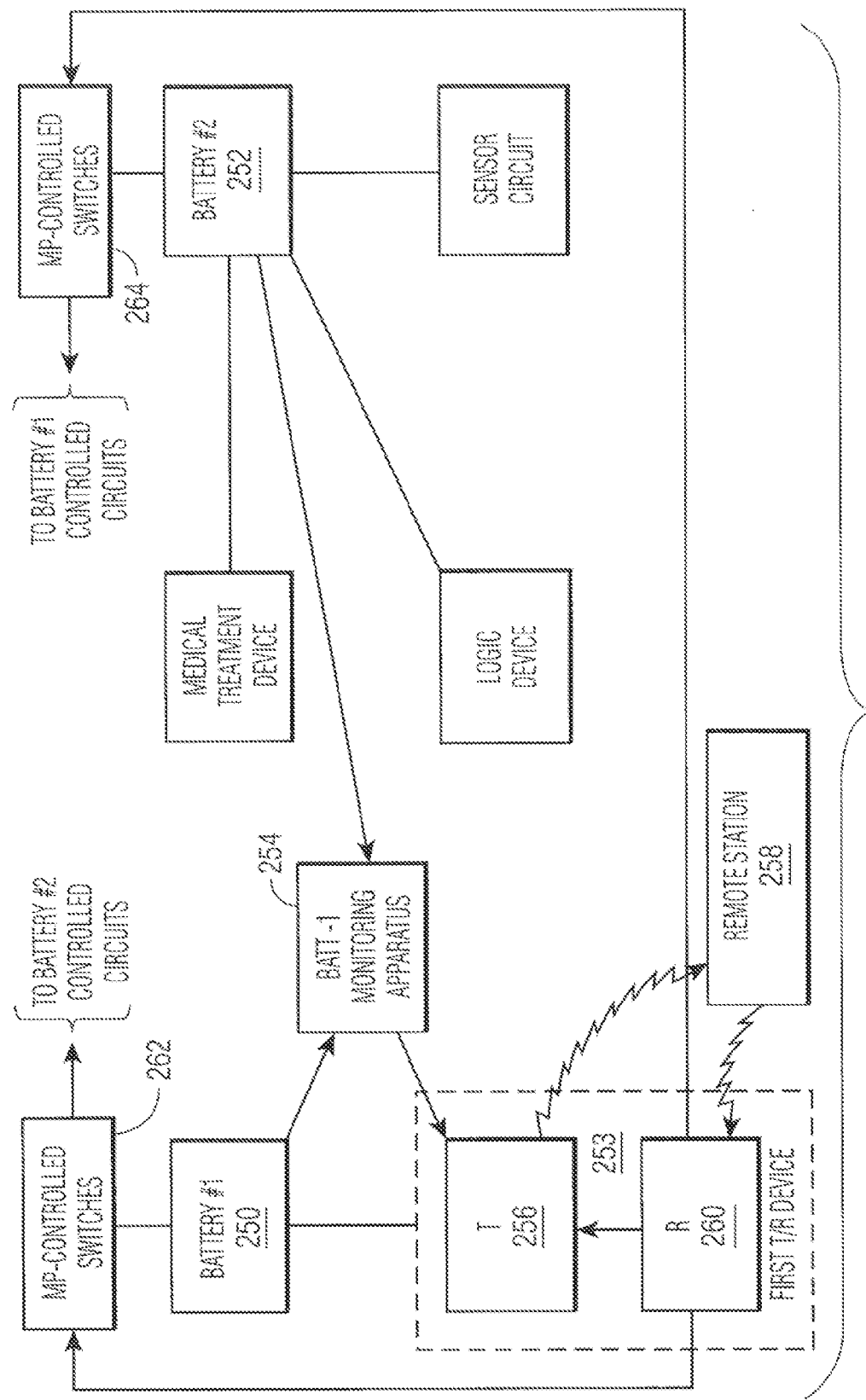
FIG. 4C is a representational block diagram showing remotely controlled power management for a remotely controllable IMD with two batteries.

FIG. 4C shows a dual power supply approach to power management. As shown in the figure, battery 252 powers the device components except for the device T/R 253 (and perhaps the battery monitoring apparatus 254), which are powered by battery 250. Battery information moves from 254 to transmitter 256 to remote station 258 for evaluation by the ME. The ME may control transmitter characteristics by sending a signal from 258 to receiver 260 to transmitter 256. In addition, the presence of a second battery gives the ME some additional options: the use of one of the batteries to perform the function of the other. Thus if battery 252, which controls the IMD in general, is nearing its end of service, and transmitter battery 250 has a substantial remaining energy supply, the ME may cause switching apparatus 262 to divert some or all of 250 energy to perform the functions intended for battery 252 (i.e. non-transmitter function). Similarly, the MP may do the mirror image diversion: In a situation with good 252 energy supply, poor 250 energy supply and the need for an urgent interaction with a ME, switching apparatus 264 may divert energy to transmitter 256 that might otherwise not have been able to be supplied by 250. The ME could learn about the status of battery 252 by information passed along the link from it to 254, and thence to 256 and 258.

Figure 4D:
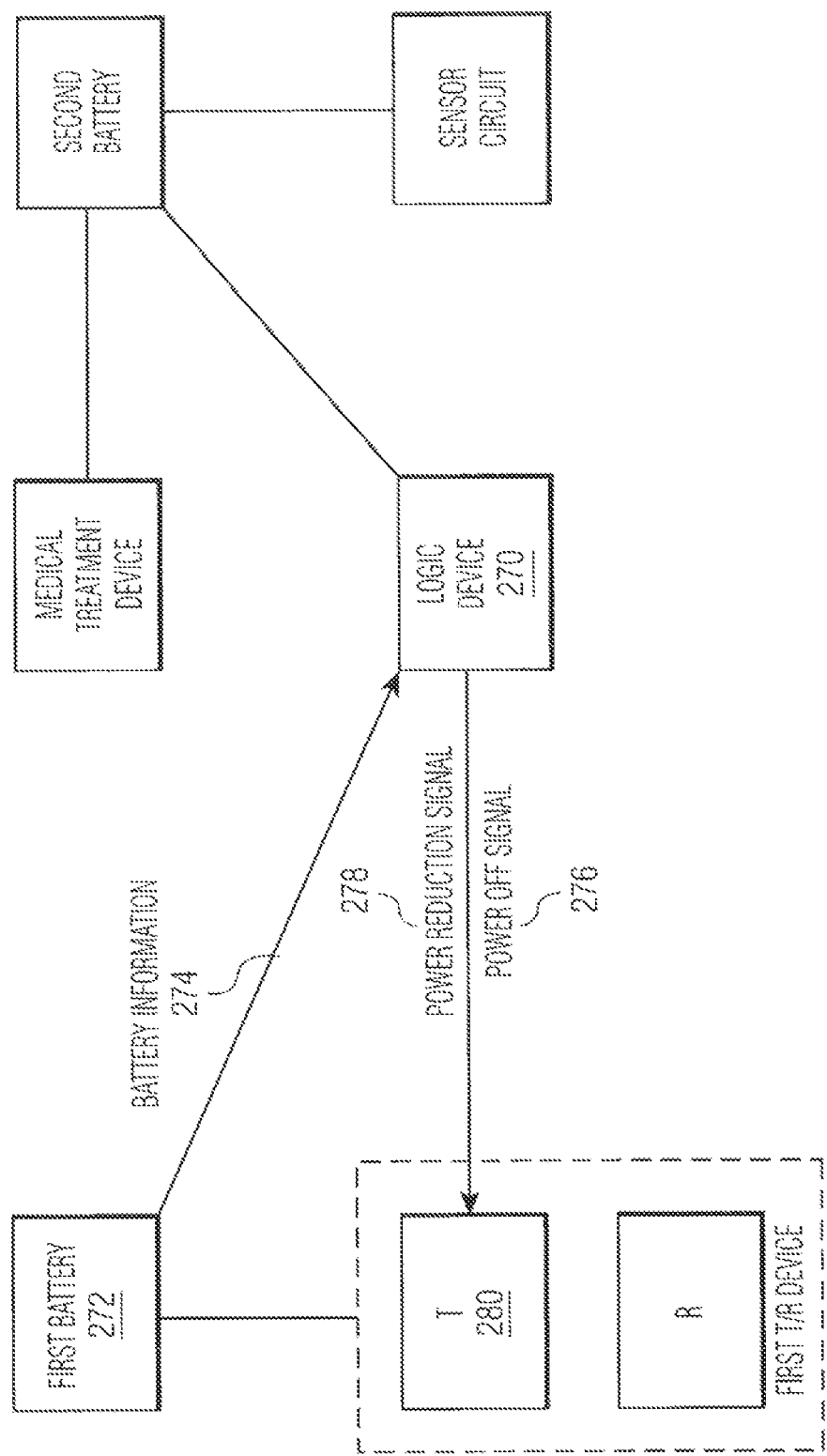
FIG. 4D is a representational block diagram showing locally controlled power management for a remotely controllable IMD with two batteries.

FIG. 4D shows a 2 battery configuration, with energy management by the IMD logic device. All of the functions performed by the apparatus in FIG. 4C could be performed by that in FIG. 4D, except that the source of management commands is logic device 270. 270 processes information 274 about the status and projected longevity of 272, and may use it to either (i) make one or more reductions 278 in the power consumption of 280, or (ii) turn off 276 the transmitter.

Figure 5A:
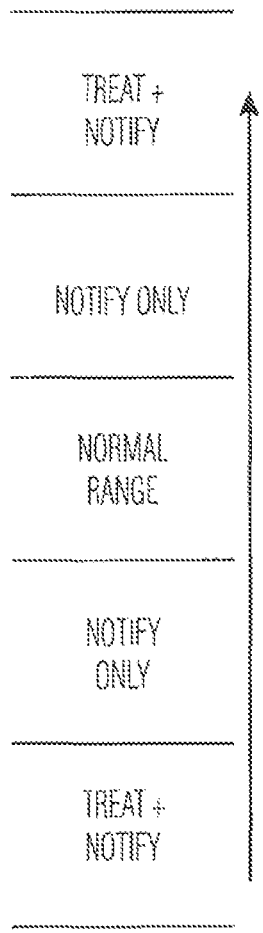
FIG. 5, which consists of FIGS. 5A and 5B, shows a graphic representation of some possible arithmetic relationships illustrating the notification definition and the parameter abnormality definition.
Figure 5B:
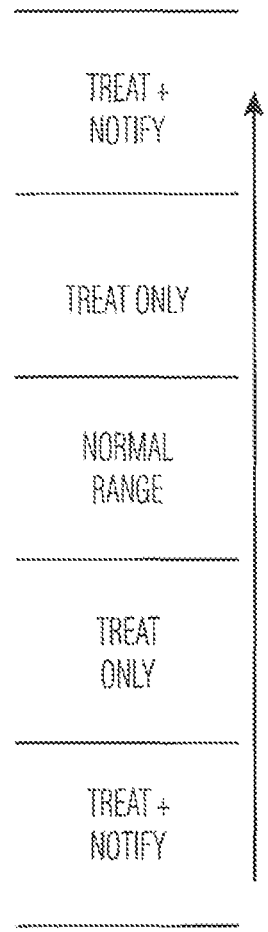

A wide variety of possible triggers for ME notification are possible. FIGS. 5A and 5B illustrate a situation in which a single parameter (e.g. heart rate) is monitored to determine device action. Conventional ICDs (which include pacemaker function) are programmed to treat tachycardias which are above a certain heart rate, and bradyarrhythmias whose rate is below a certain heart rate. The scenario illustrated by FIG. 5A shows a scenario in which a range of rates which is intermediate between the high rate, at which treatment is definitely required, and the normal rate, may be defined as the notification range of rates. For example, an ICD might be programmed to:

a) notify for rates from 140 to 160 bpm and to treat and notify for rates above 160 bpm. The ME, upon notification, would decide whether treatment is required for a rate of say, 150 bpm, and if so, cause the ICD to provide such treatment. The ME might decide (a) to try some gentle treatment such as a non-aggressive anti-tachycardia pacing for the situation, (b) to go ahead and provide aggressive treatment, or (c) to not treat at all. In the latter case, the ME might decide to check the patient at some later time, e.g. by leaving an instruction in the ICD for the ICD to check in with the ME in 30 minutes. The ME might further program altered "second notification" criteria, i.e. if the rhythm normalizes, then over the next 24 hours, the threshold for notification is lower (e.g. 130 bpm).

b) notify for rates from 140 to 160 bpm and to treat (and not notify) for rates above 160 bpm. [This is not shot in the figure.] This saves battery in cases where there is little or no uncertainty about which therapy is the appropriate one.

In the figure, a similar format is programmed for bradyarrhythmia. For example, the pacing circuits may treat when the rate declines to 40 bpm, but may be programmed to notify for rates in the range of 40 to 50 bpm. Alternatively, the programming person might choose not to notify for pacing at 40 bpm (i.e. treat without notification).

FIG. 5B shows a format in which the ME is notified (and treatment is given) for values of a parameter that are extreme but not for values that are only moderately abnormal. For example, the ME might be notified for tachycardia that was treated whose rate was 260 bpm, but not for tachycardia which were treated with rate less than 200 bpm.

The aforementioned scenarios reflected by FIGS. 5A and 5B concern rather simply notification criteria. More complex ones may depend on the results of multiple different parameters from multiple sensors, and their evolution over time. Still more complex scenarios may depend not just on the measured values of these parameters, but complex mathematical functions of them.

Figure 6A:
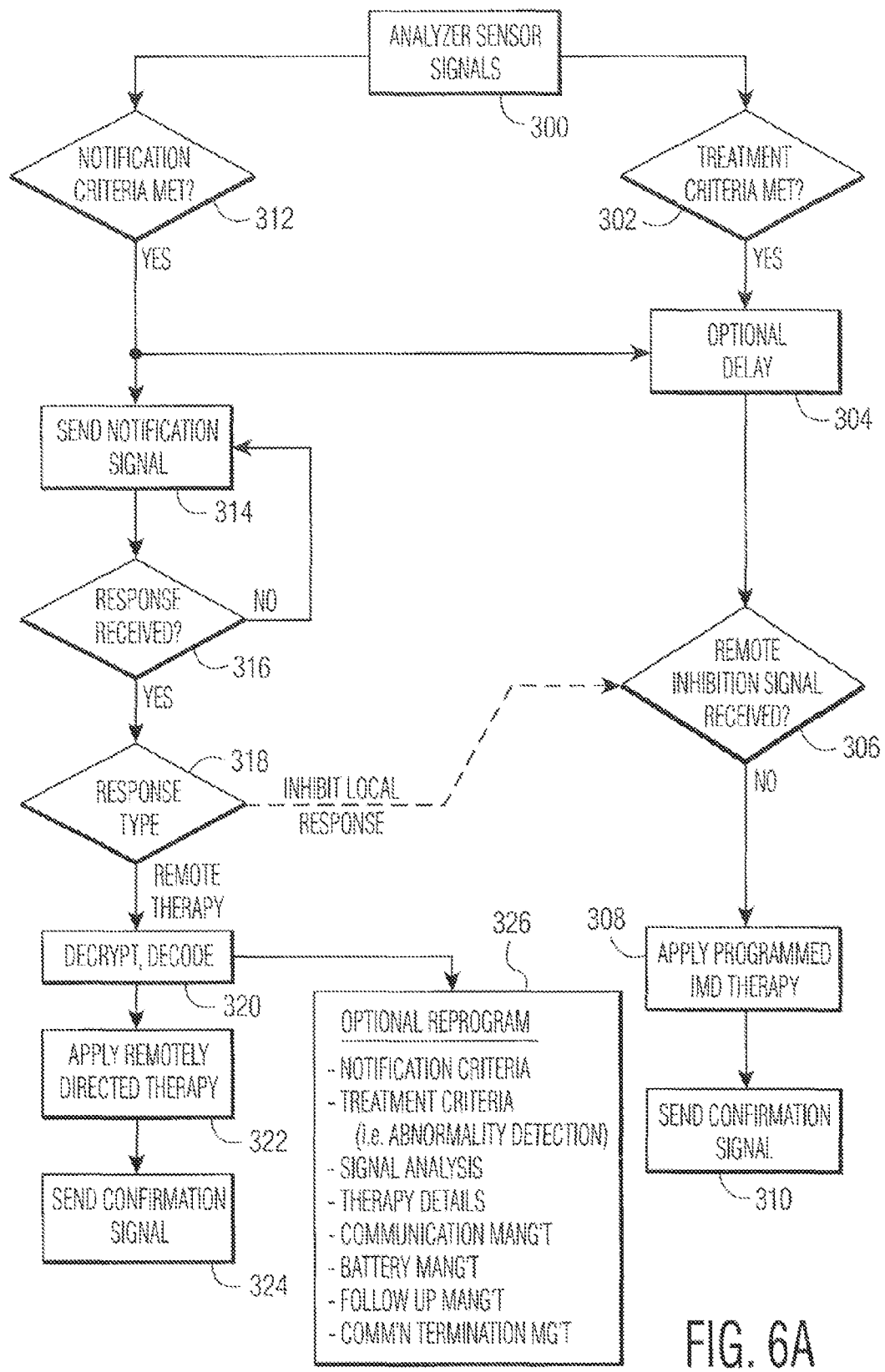
FIG. 6A shows a flow diagram of one possible algorithm for notification.

Once notification has occurred, the other dimension of interaction between the IMD and the ME, is how much control the ME has access to, following notification. FIG. 6A shows a scenario in which the ME is given essentially complete control. The right hand side of the figure shows the essential features of operation when the device operates autonomously. Following detection of a parameter value 302 which requires therapy, the device applies the pre-programmed therapy 308, and optionally transmits a confirmation signal, block 310, indicating that therapy has been provided. However, if notification criteria have been met, 312, the IMD sends a notification signal, 314, for receipt by a remote station, and awaits a response, 316. Once the ME is in communication with the IMD, the ME may both positively and negatively control the device; That is, the MEP may choose to inhibit (block 318 to 306) an action that the device, if operating autonomously, would have performed. Alternatively the ME may choose to cause the device to deliver therapy, even though the IMD program may not have called for this. In such a circumstance, block 318 leads to 320, in which an ME command is decrypted and decoded, and then to 322, in which the therapy instructions are carried out, followed by the sending of confirmation signal 324.

Since the establishment of a communication link between the ME and the IMD may take a short time, an optional delay 304 is added in before the IMD acts autonomously, in a situation when notification has occurred. This is indicated by block 312 inducing optional delay 304, to prevent autonomous IMD therapy before the ME can be involved.

The ME has a number of options for influencing the management of future events post notification, shown in block 326. In a preferred embodiment of the invention, the ME may reprogram (a) notification criteria, (b) the definition of what constitutes and abnormality, in terms of autonomous device functioning, (c) aspects of sensor signal analysis, (d) the details of therapy during autonomous device functioning, (e) communication management [route, mode, channel, etc.], (f) battery management, (f) follow-up management (the ability of the ME to ask for a callback from the IMD) after a ME-managed-event, to report patient status), and (g) communication termination management (e.g. how long until communication ends after [i] a successfully managed event, and [ii] an event in which communication failed during the event).

Figure 6B:
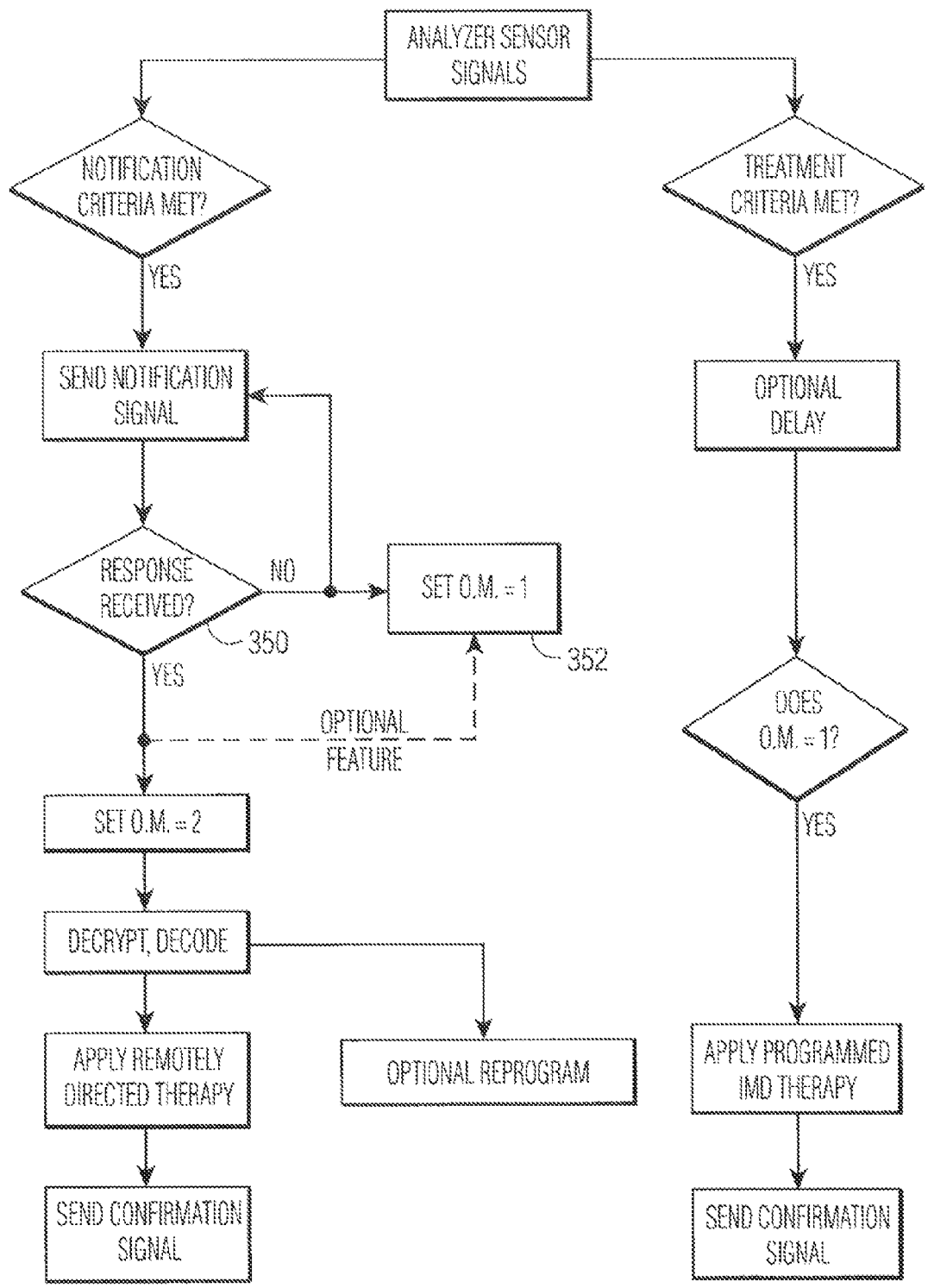
FIG. 6B shows another flow diagram of one possible algorithm for notification.

FIG. 6B shows another management scenario. Two operating modes are defined for the IMD. In a first operating mode (O.M.=1, in the figure) the IMD logic device is in control of therapy, while in a second operating mode (O.M=2, in the figure), the ME is in control. The scenario shown in 6A involved moment to moment choices by the ME of whether to inhibit an IMD function; In the scenario in 6B, all IMD function is inhibited in the second operating mode, unless (a) the ME chooses to return the control to the IMD (block 350 to 352 via broken line indicating optional feature), or (b) communication fails [350 to 352 via solid arrow]. In other aspects not explicitly mentioned, the algorithm in FIG. 6B is identical to that of 6A.

Figure 6C:
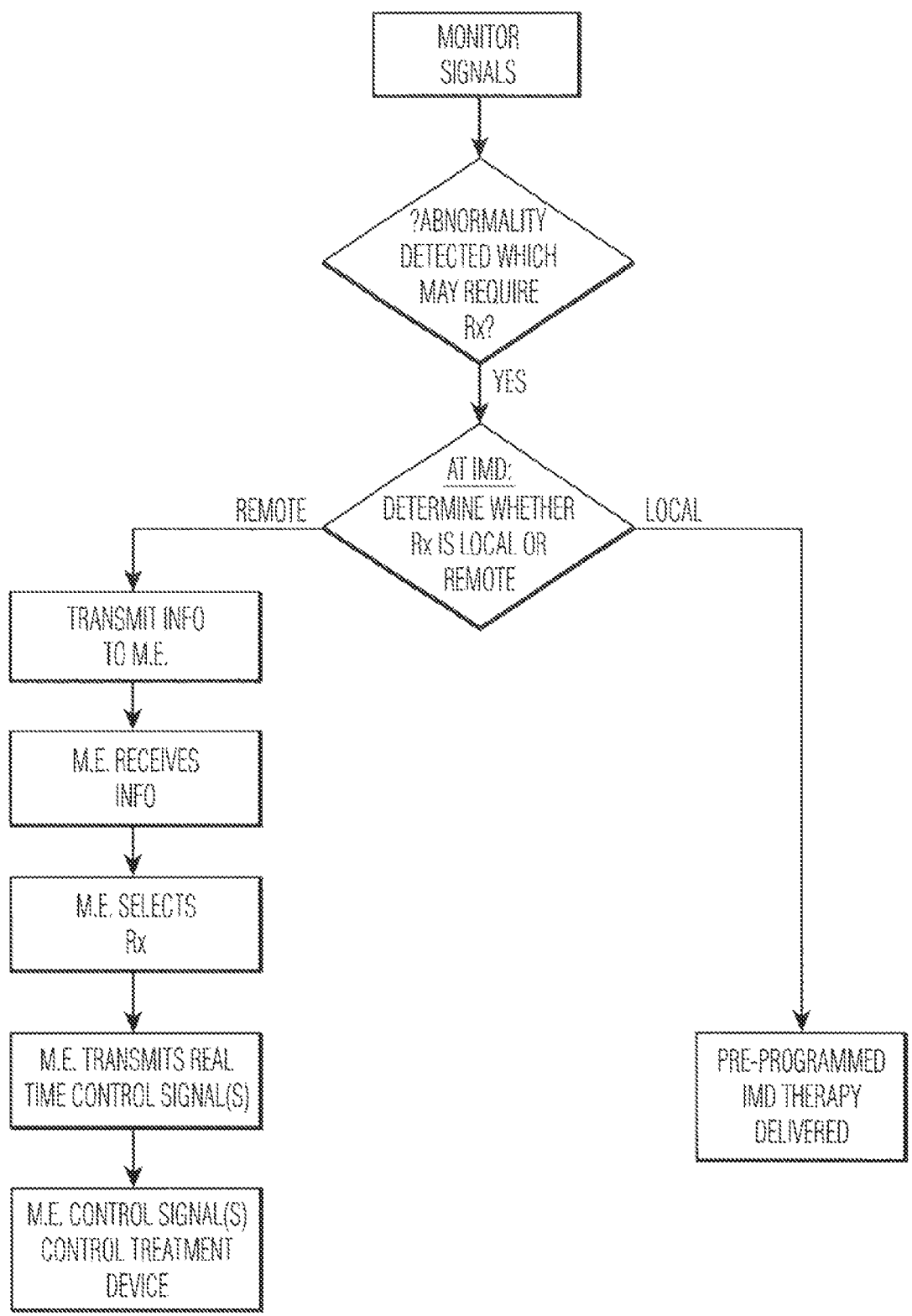
FIG. 6C shows another flow diagram of one possible algorithm for notification.

FIG. 6C shows a different algorithm. In this case, the decision between remote and local management is made (a) early on [i.e. before the ME is involved], and is made by the logic device of the IMD. Other aspects of the figure not specifically discussed are similar to those in already discussed figures.

Figure 6D:
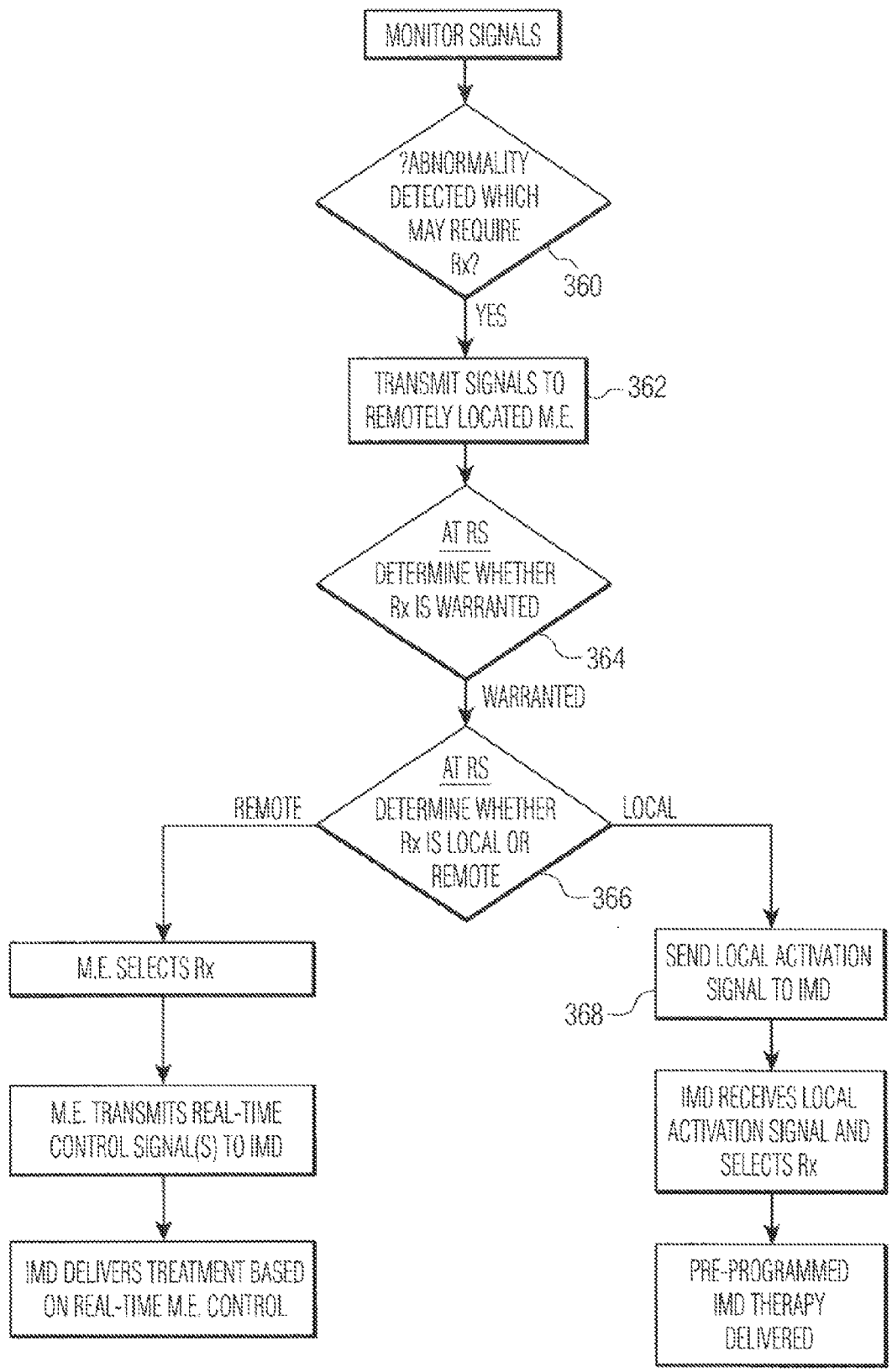
FIG. 6D shows another flow diagram of one possible algorithm for notification.

FIG. 6D shows another algorithm in which the remote station (RS) is given a particularly high level of priority. If an abnormality is detected by the IMD which may require treatment 360, signals are transmitted to the ME 362, at which point, two determinations are made: (a) Is therapy warranted [block 364]? and (b) Is the source of therapy-related choices to be local (i.e. the IMD) or remote (i.e. the ME) [block 366]? If the source of therapy is to be local, the ME returns control to the IMD. Other aspects of the figure not specifically discussed are similar to those in already discussed figures.

Other scenarios in which the ME does not have top priority have been discussed hereinabove.

Figure 7:
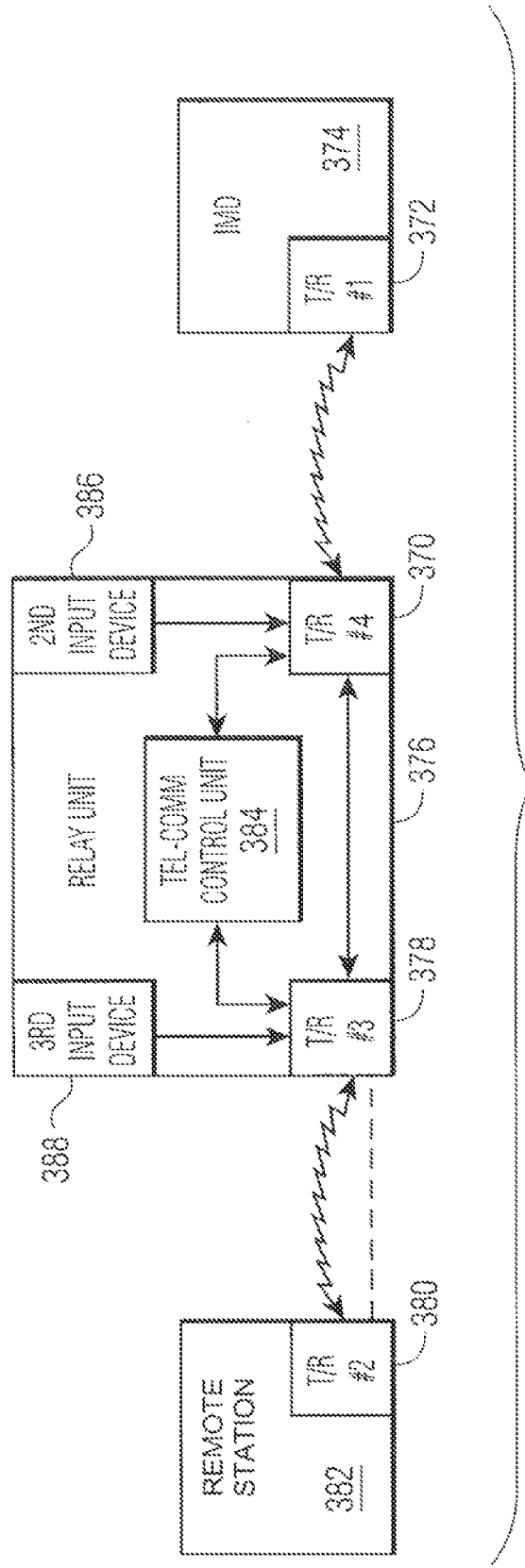
FIG. 7 shows a representational block diagram of a communications relay and its links to an IMD and a remote station.

Since battery conservation is a major concern with IMDs, and since wireless communication is a feature, the most efficient way to manage such devices is to provide one or more relay units between the IMD and the ME. Having one such unit in close proximity to the IMD will help to limit IMD battery depletion. Many possible relay units may be designed, and are known in the art. The essential features of such a unit are shown in FIG. 7. A fourth transmitting and receiving device, "fourth T/R" 370 communicates wirelessly with the first T/R 372 of the IMD 374. 370 is linked within relay unit 376 to a third T/R 378. The communication of the third T/R with the remote station 382 is via the second T/R 380. The communication between 378 and 380 may be wired (broken line) or wireless. It may involve no intervening communication device, or a number of such devices. It may involve a public telephone carrier or a private network, and may involve the Internet.

376 contains telecommunications control unit 384, which may adjust the operating characteristics of the third T/R to optimize communication with the remote station, and adjust the operating characteristics of the fourth T/R to optimize communication with the IMD. An optional second input device 386 could allow a local person or the patient to have some or complete control of the IMD; An optional third input device 388 could allow a local person or the patient to send a signal (e.g. a notification signal) to the ME. This could be used in a case where the patient feels that observation and potential ME intervention is warranted.

The following description details a preferred embodiment of the invention, entailing an ICD as the IMD. "MP" refers to a medical professional, which is the human version of the aforementioned ME.

Hereinabove and hereinbelow, ICD is intended to include:
A) devices which can administer a defibrillation shock; and
B) devices which can administer a defibrillation shock and can administer cardiac pacing. It is to be understood that this technology may be used in any implantable medical device, and any remotely controlled critical system.

FEATURES OF THE INVENTION

1) The Implantable Cardioverter Defibrillator ("ICD") may initiate the communication between itself and the Central Station ("CS."). Mechanisms for this are illustrated.

2) The "control unit" referred to in Ser. No. 10/460,458 may be:
A) a cellular telephone or other personal communication devices (such as a Blackberry®) as are known in the art.
B) the Stationary Unit referred to in Ser. No. 10/460,458; and
C) any relay unit whose purpose is to amplify the signal as it is passed along between ICD to CS, Hereinbelow, the unit which serves as the communications hardware link between the CS and the ICD shall be referred to as the repeater unit ("RU").

3) Means within the ICD may select alternate mode of communication (e.g. a public or private telephone network, or the internet) and may select alternate routes of communication (e.g. in a multi-segment communication, selecting each segment of the total communications link.

4) Handshake signals may be exchanged between:
A) the CS and the RU;
B) the RU and the ICD; and
C) the CS and the ICD.

The handshake signals may be used to indicate the presence or absence of communication signals between two components (e.g. the ICD and the RU) or to indicate the quality of the signals.

5) If the handshake signals indicate either an absent communications link or a poor quality one, the handshake signals may be used to cause the ICD to:
A) select an alternate mode of communications;
B) select an alternate route of communications;
C) increase the power output of the ICD transmitter;
D) increase the sensitivity of the ICD receiver.

6) The communications route from the ICD to the CS may involve multiple segments. These segments may include:
A) an ICD to RU segment;
B) one or more RU to RU segments;
C) a RU to CS segment; and/or
D) a direct ICD to CS segment.

7) Ser. No. 10/460,458 presents two formats for ICD control by a remotely located medical professional ("MP"):
Format A) In one (claim 219 and the 24 dependent claims which follow), the MP has primary control, and, in the absence of proper communication between the ICD and the MP, the ICD is in control;
Format B) In the other (claim 244 and the 25 dependent claims which follow), the ICD has primary control. The MP may overrule the ICD on a therapy decision, if he deems this to be desirable.

Feature 7 presents an approach in which the choice between Format A and Format B may be:
A) "hardwired" into the ICD;
B) irreversibly programmable (using a PROM, EPROM, EEPROM, etc., as is known in the art)
C) programmable by the medical professional who is responsible for programming the patient's ICD on a routine basis;
D) programmable by the MP, at the time of a medical emergency which has caused the ICD to communicate with the MP; and/ or
E) programmable by the ICD, at the time of a medical emergency which has caused the ICD to communicate with the MP.

8) When the ICD initiates a communication with the CS, there may be a 2-or-more tier format such that:
A) 2 or more levels of emergency are defined;
B) for each level, a greater degree of "communications aggressiveness" (on the part of the ICD) is defined.

For example:
2 levels of emergency:
Moderate emergencies include ventricular tachycardia ("VT") at rates less than 160;
Major emergencies include a) VTs at rates greater than or equal to 160 and b) VTs or ventricular fibrillation ("VF") requiring a shock.

The corresponding two levels of communication aggressiveness would be:
For Moderate emergencies: a) no ICD transmitter output power boost (see below); and b) a small number of repeat attempts by the ICD to contact the CS; and
For Major Emergencies: a) one or more ICD transmitter output power boosts; and b) a large number of repeat attempts by the ICD to contact the CS.

Examples with 3 or more levels are obvious.
There is also the possibility of moderate emergencies (or the lowest level of emergency in a three or more level setup) resulting in no attempt at communication by the ICD.

9) Referring to 8) above, the definition of each level of emergency may be:
A) "hardwired" into the ICD;
B) irreversibly programmable (using a PROM, EPROM, EEPROM, etc., as is known in the art)
C) programmable by the medical professional who is responsible for programming the patient's ICD on a routine basis;
D) programmable by the MP (after communication between the MP and the ICD has been established), at the time of a medical emergency which has caused the ICD to communicate with the MP; and/or E) programmable by the ICD (after the event which calls for a communication between MP and ICD); and/or F) programmable by the ICD (during the event which calls for a communication between MP and ICD), if ICD circuitry determines that battery conservation requirements dictate a shut-down of the communication link.

10) Options based on battery reserve of ICD:

If hardware/software within the ICD determines that the ICD battery reserve is low, ICD options include:

A) terminate the communication;

B) send a message to the MP indicating the low reserve, and then terminate the communication;

C) lower power output and attempt to continue the communication; (This step may be repeated one or more times.); and/or D) continue the communication with output as is, and repeat assessment at a future time.

11) End of communication options:

The communication may end:

A) because of low ICD battery reserve, see Feature 10), above;

B) because the MP determines that further communication is not warranted; and/or C) because the ICD logic unit determines that further communication is not warranted.

12) Identification—related issues:

Privacy in the communication between the ICD and the MP to be maintained:

A) Encryption and decryption per means and methods:
i) in Ser. No. 10/460,458; and
ii) other, known in the art;

B) An identification system wherein any ICD requires proof of MP identification, before and during and communication session.

13) The download of contingency plans from MP to the ICD, as soon as possible after the exchange of information begins. The purpose of the contingency plan download is to have a management strategy in place within the ICD, should the ICD-MP communication get interrupted midway through the event. Although the basic system calls for the ICD to revert to its programmed behavior in the event of communications interruption, the MP may desire to leave a temporary plan in place, to be used for the remainder of the current medical event. The MP may update the contingency plan as needed, as the medical event progresses.

An example of such a contingency plan would be more aggressive (or less aggressive anti-tachycardia pacing, prior to defibrillator shock). Another example would be to eliminate all intermediate energy shocks, and deliver only high energy shocks. Numerous other examples will be apparent to those skilled in the art.

Figure 8:
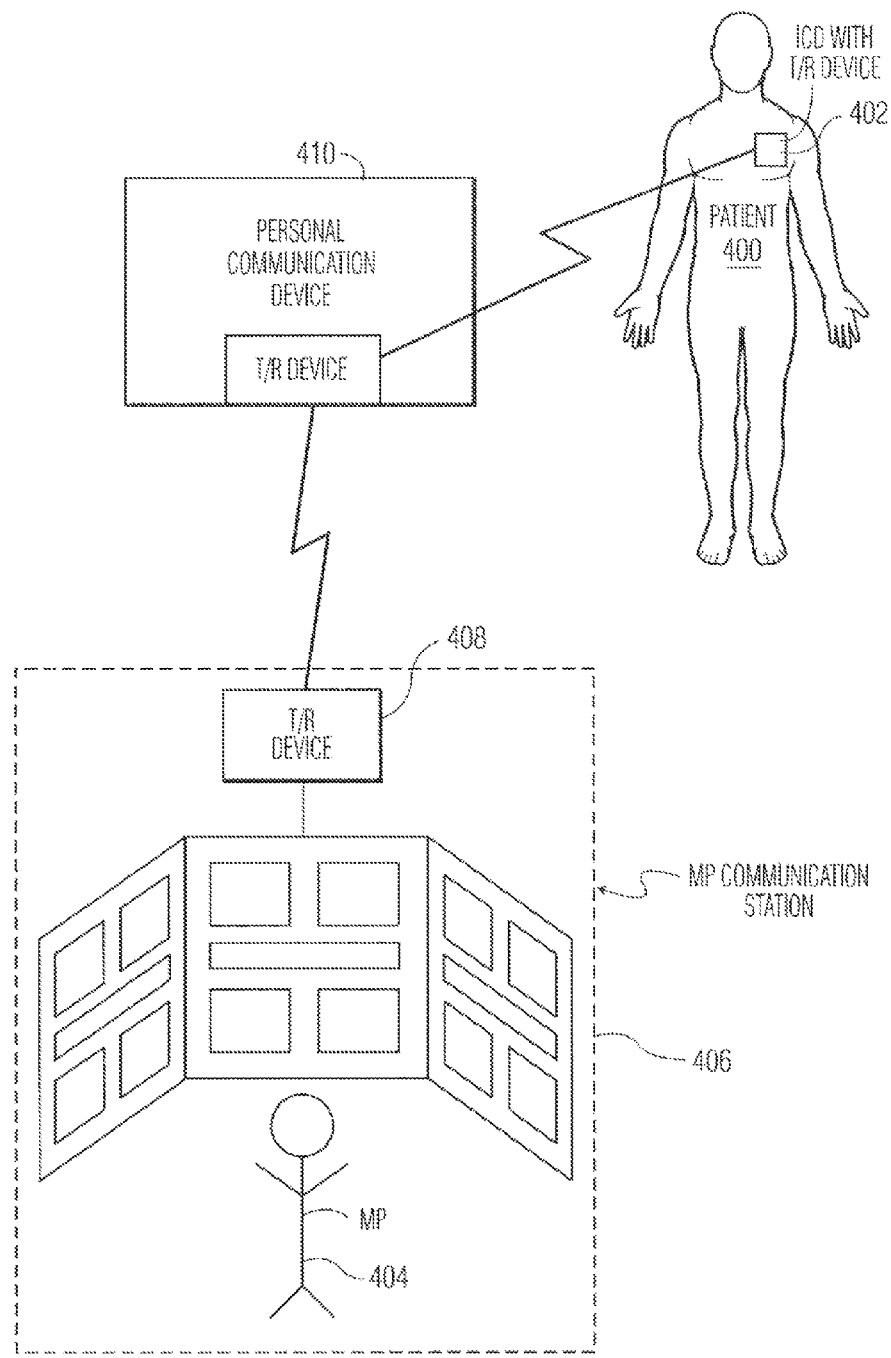
FIG. 8 show shows an overview of one approach to ICD management.

Referring to the figures, which show additional documentation of the means and methods of accomplishing the above 13 features:

FIG. 8 shows a patient 400 with and ICD 402 which communicates with a MP 404 at a MP communication station 406. 406 may be a central station as described in Ser. No. 10/460,458 or a central or peripheral station as described in Ser. No. 11/502,484. The ICD antenna is not shown, but in FIGS. 8-10, it is to be understood that the ICD has one or more antenna which allows it to properly communicate.

The communication route is in either direction between:

A) the T/R device within the ICD; B) the T/R device within personal communication device 410; and C) the T/R device within the MP communication station.

The communication route may also be directly between the T/R device within the MP communication station and the T/R device within the ICD.

Figure 9:
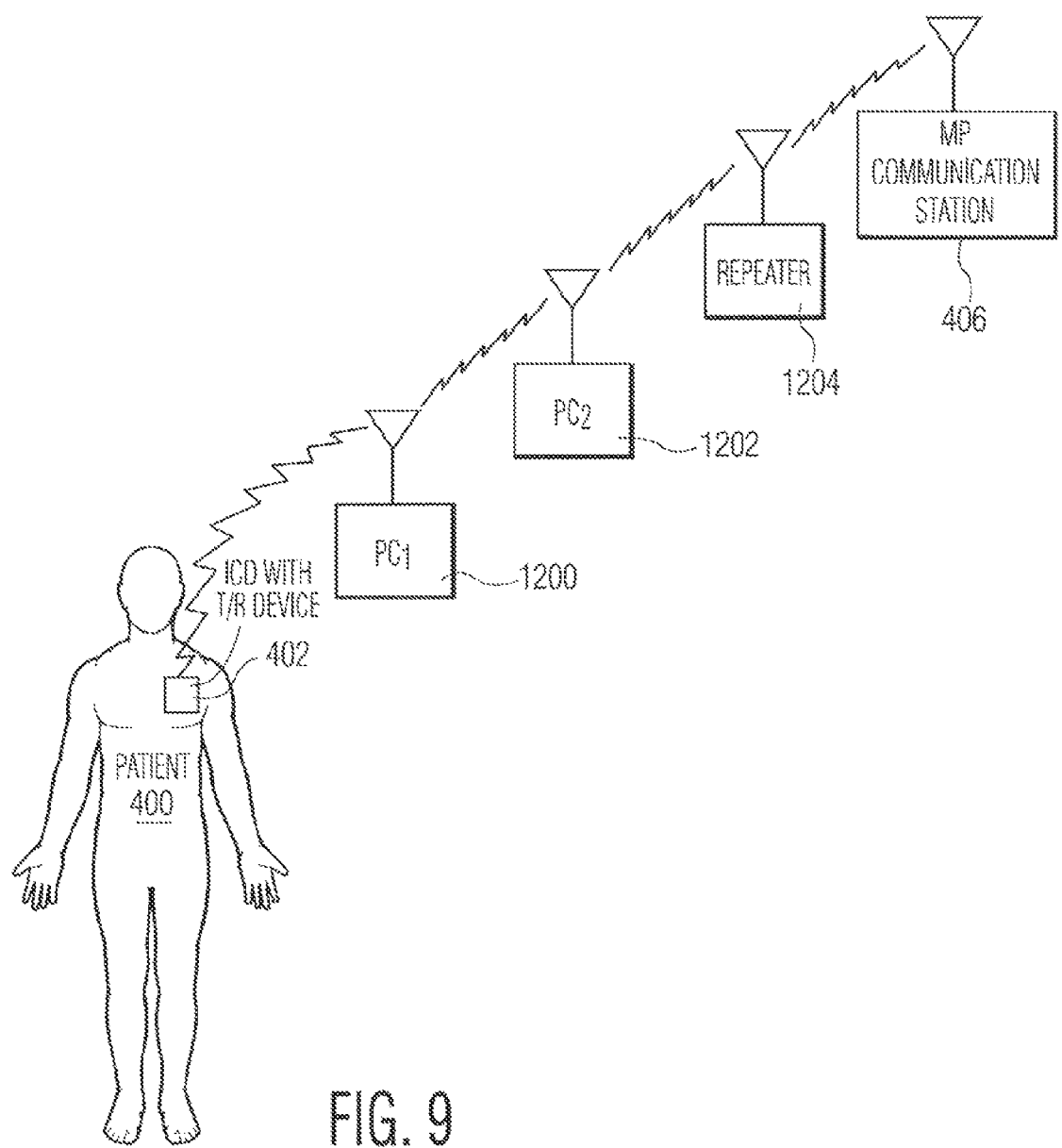
FIG. 9 shows a representational diagram of communication with multiple relays.

Referring to FIG. 9: It is also possible to have two or more intermediate communication links between the ICD T/R and the T/R of the MP communication station. In FIG. 9, there are 2 personal communication devices 1200 and 1202 and a repeater unit 1204 (as discussed above). Possible arrangements include:

A) two or more personal communication devices and no repeater units; B) one or more repeater units and no personal communication devices; and C) one or more repeater units and one or more personal communication devices.

It is also possible that the communications route would change during a single medical event. This would occur if either the MP or the hardware/software within the ICD determines that a change of route is desirable.

The antenna shown for 406 may, at times, not be used, since at times, communication with 406 may be via "land line."

Figure 10:
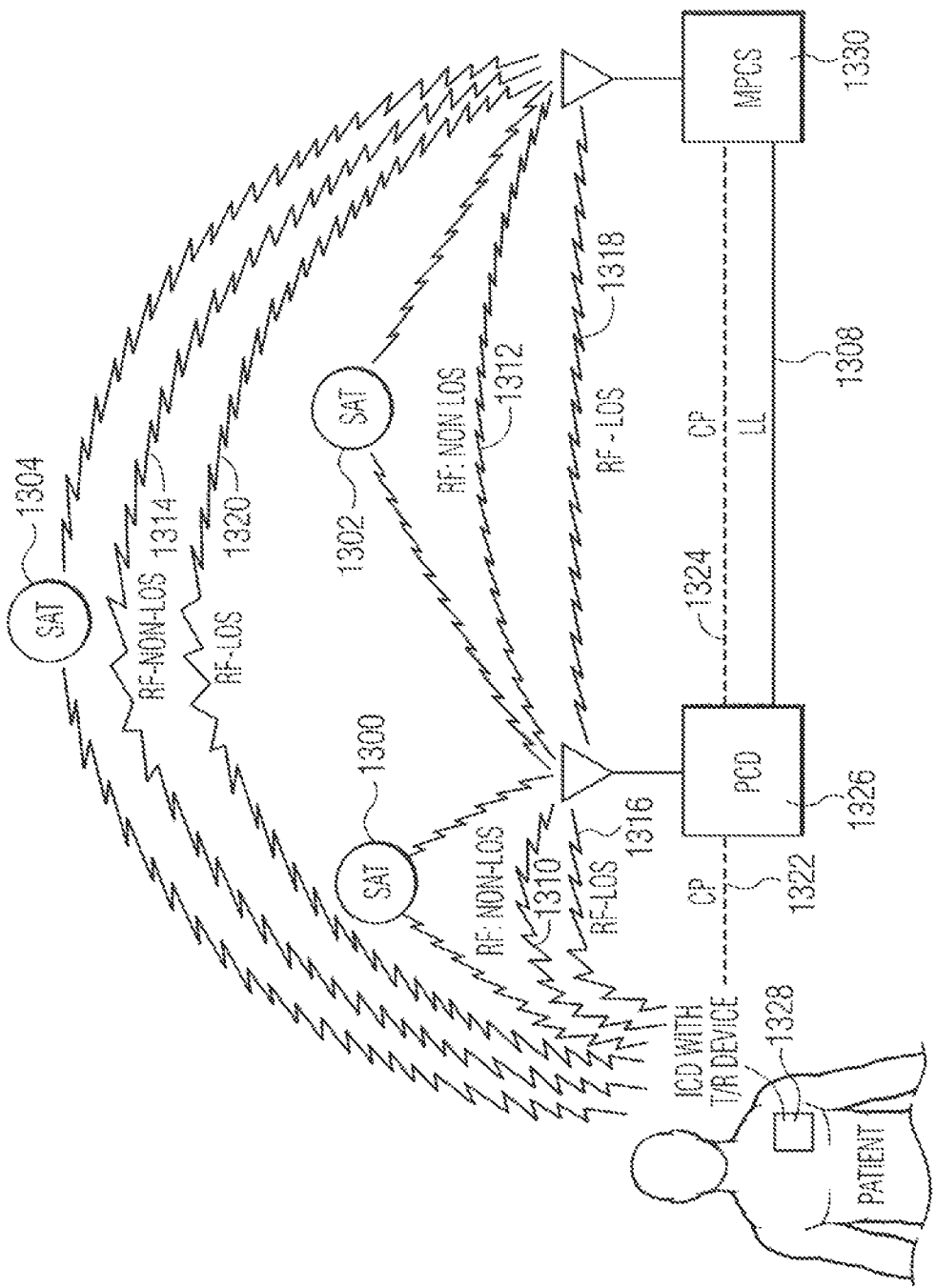
FIG. 10 shows a representational diagram of ICD communication via a personal communication device.

FIG. 10 shows that each segment of the communication route may be:

A) via satellite(s) (1300, 1302 and 1304 in the figure, each of which may represent a single satellite or an array of multiple ones); B) via a non-line-of-sight radiofrequency link (1310, 1312, 1314); C) via a line-of-sight radiofrequency link (1316, 1318, 1320); D) via a public or private telephone network; E) via cell-phone and/or personal communication device network (1322, 1324); F) in the links beyond the ICD link, via "land lines 1308;" and/or G) combinations of A-F.

The PCD 1326 in figure PCD in FIG. 10 may be replaced by a wireless router such that the communication between the ICD and the MP is ICD 1328.rarw..fwdarw.wireless router-.rarw..fwdarw.internet.rarw..fwdarw.MP communication station 1330. The route from the wireless router to the communication station can have a wide variety of configurations, as is known to those skilled in the art.

Figure 11:
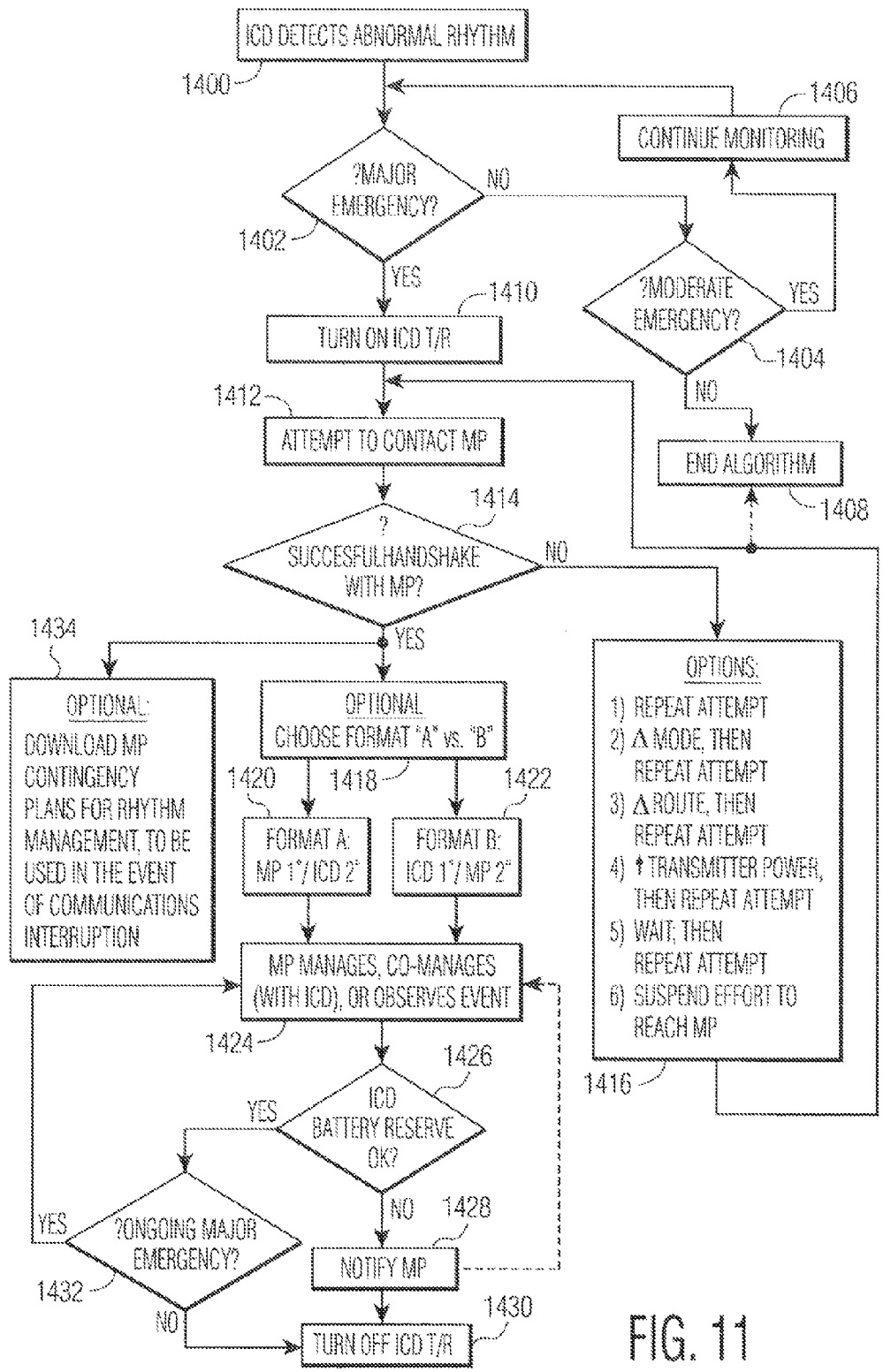
FIG. 11 shows a flow diagram of an ICD management algorithm allowing remote notification and management.

FIG. 11 shows one possible algorithm for allowing the ICD to communicate with a MP communication station, with or without an intervening repeater unit/cell phone/stationary unit/control unit.

If/when the ICD detects an abnormal heart rhythm that requires action, may require action or require analysis, block 1400, it determines whether the rhythm requires communication with the MP. One method of determination is to classify rhythm abnormalities as either major or not major, and to communicate if the rhythm abnormality is major. This determination is made at block 1402.

The figure shows a setup with two levels of emergency, as described in Feature 8, hereinabove. If the rhythm is determined, block 1402, not to be a major emergency, but is a moderate emergency, block 1404, then continued monitoring, bock 1406, is in order, to monitor for the possibility of the event turning into a major emergency; If this occurs, return to block 1402, and proceed with major emergency section of the algorithm. If there is neither a major nor a moderate emergency, block (either because the emergency condition has resolved, or because there is an abnormality which is less urgent than even the moderate category), the algorithm shown in FIG. 11 ends. ICD monitoring, of course, continues as always.

If a major emergency is detected, block 1410, the ICD T/R is turned on. Not leaving it on continuously saves the battery charge. The ICD then attempts to contact the MP, block 1412. A handshake protocol, which may have some or all elements of that described in Ser. No. 10/460,458 or may have one or more features of other handshaking protocols as are known in the art, ensues, block 1414.

If the handshake is unsuccessful, or (optionally) if the quality of the handshake is sub-optimal, block 1416 lists six possible options. These include:

1) repeat attempt at handshake, using the same communication parameters;

2) change communication mode (as defined m Ser. No. 10/460,458) and repeat handshake attempt;

3) change communication route (as defined in Ser. No. 10/460,458) and repeat handshake attempt;

4) increase ICD transmitter power and repeat handshake attempt;

5) wait, and then repeat the handshake attempt, either with the same transmitter/mode/route parameters or one of more altered ones; and/or 6) suspend efforts to contact the MP.

In the case of the options 1-5, block 1416 leads to block 1412: a repeat attempt to contact the MP.

In the case of option 6, block 1416 leads to 1408 and the algorithm ends. Option 6 may be selected after a pre-programmed number of attempts to reach the MP has occurred. Alternatively, the number of attempts may not be pre-programmed and may depend on the ICD battery status (see hereinbelow), or the level of the emergency. If the handshake is successful, than the MP will have the opportunity to participate in the management of the emergency. The format for such participation is:

a) pre-programmed Format A (MP control is primary; ICD control is in the event of communications interruption);

b) pre-programmed Format B (ICD control is primary; MP control in the event that the MP chooses to override the ICD decision);

c) either Format A or Format B, with the choice made by the MP at the time of the event; or d) either Format A or Format B, with the choice made by the ICD based on the severity of the event.

As indicated hereinabove, the aforementioned Format selection is made, block 1418, leading to either Format A/block 1420, or Format B/block 1422. Thereafter the MP either manages, co-manages (with the ICD) or observes the emergency event, block 1424. The communication between the ICD and the MP may terminate in one of three ways:

A) by necessity, because the ICD battery has reached a point in its discharge, where it is deemed unwise to continue communications;

B) due to the heart rhythm-related emergency having been resolved; or

C) due to an unintended interruption of communications.

In the event of A), block 1424 leads to 1426, which leads to a MP notification, block 1428. This may be followed by:

1) The ICD immediately turning off its T/R, block 1430;

2) The MP deciding to immediately turn off the ICD T/R, block 1430, or, 3) block 1424, the MP deciding to take some additional time to communicate, despite the low battery warning.

Algorithms which omit the warning to the MP of impending ICD T/R shutoff are possible.

In the event of B), block 1424 leads to 1426, which leads to 1432, which leads to 1430.

In the event of C), attempts to re-establish communication occur, as described in Ser. No. 10/460,458. During the time when communication has not been established, the ICD logic unit manages the case.

To avoid a situation where the ICD logic unit must takeover in the middle of an event which the MF was managing in a different manner than would have been executed by the logic unit, the MP may, from time to time download contingency plans to the ICD, block 1434, such that, in the event of an interruption, the ICD has enough of the current MP decision making algorithm to complete the management of the event. This approach is discussed hereinabove, as Feature 13.

The invention claimed is:

1. A system of electronic medical apparatus for treating a human patient, comprising at least one implantable medical device (IMD) adapted to be implanted in said patient, which may be alternatively automatically self-controlled and remotely controlled by a medical expert, said apparatus comprising, in combination:

(1) a least one IMD comprising, in combination:

(a) a first transmitting/receiving (T/R) device for transmitting medical data sensed from said patient to, and for receiving at least one remote control signal from, a remote station;

(b) an electronic medical treatment device for treating said patient in response to control signals applied thereto;

(c) a sensor circuit, having a sensor circuit output, for producing at least one sensor circuit output signal at said sensor circuit output in response to the medical data sensed from the patient; and (d) a logic device coupled to each of (i) said sensor circuit output, (ii) said first T/R device, and (iii) said treatment device, for (i) analysis of said at least one sensor circuit output signal, (ii) generating a remote station notification signal, (iii) generating at least one local treatment device control signal, and (iv) generating at least one remote treatment device control signal, in response to said received remote control signal;

wherein:

said logic device analyzes said at least one sensor circuit output signal to detect a medical abnormality which requires notification of the medical expert at the remote location, and is operative to generate a notification signal, for consideration by said medical expert when said analysis reveals said medical abnormality;

upon receipt of said notification signal, said first T/R device transmits said notification signal representing at least one medical state of said patient to the remote station;

said logic device analyzes said at least one sensor circuit output signal to detect a medical abnormality which requires treatment and is operative to generate at least one local treatment device control signal, if required;

said logic device is operative to generate at least one remote treatment device control signal in response to said at least one remote control signal received from the remote station by said first T/R device;

said logic device determines whether to issue a notification signal, to issue a local treatment signal, to issue both a notification and a local treatment signal, or to issue neither a notification nor a local treatment signal, based on said analysis; and (2) a remote station comprising, in combination:

(a) a display device for displaying medical information from said patient for evaluation by said medical expert at the remote station, in response to the receipt of said notification signal transmitted from said at least one IMD;

(b) a first input device, responsive to said medical expert, for producing at least one remote control signal for controlling said IMD; and (c) a second T/R device, coupled to said display device and said input device, for receiving said notification signal and for transmitting said at least one remote control signal;

wherein:

said medical expert observes and analyses said information representing at least one medical state of said patient via said display device, following receipt of said notification signal, based on said analysis, said medical expert may cause said input device to generate said at least one remote control signal; and (3) a communication relay unit including:

(a) a third transmitting/receiving (T/R) device for electronic communication with said second T/R device of said remote station; and (b) a fourth transmitting/receiving (T/R) device, coupled to said third T/R device, for electronic communication with said first T/R device of said IMD;

wherein:

said notification signal is transmitted from said first T/R device of said IMD sequentially via said fourth T/R device and said third T/R device to said second T/R device of said remote station; and said at least one remote control signal is transmitted from said second T/R device of said remote station sequentially via said third T/R device, said fourth T/R device and said first T/R device to the logic device of said IMD;

whereby said IMD communicates with said remote station through said relay unit; and said IMD delivers therapy, if required, in response to one of said at least one local treatment device control signal and said at least one remote treatment device control signal.

2. The apparatus defined in 1, further comprising a plurality (x) of communication relay units, each including:

(1) a (y)th transmitting/receiving (T/R) device;
(2) a (y+1)th transmitting/receiving T/R device;

wherein (a) y=2z+1;
(b) z is an integer which is at least the number 1 and at most the number x;
(c) said first T/R device and said second T/R device are linked by x+1 separate communication links serially connected through said x communication relay units, as follows:

(i) a (p)th one of said T/R device, where p equals one of the possible values of y, belonging to the [(p−1)/2]th communication relay unit, communicates with said second T/R device;

(ii) said (p+1)th T/R device, belonging to said [(p−1)/2]th communication relay unit, communicates with one said (qth) T/R device, belonging to said [(q−1)/2]th communication relay unit, where q equals one of the possible values of y except p;

(iii) step (ii) is repeated, with each successive step utilizing a remaining communication relay unit, until all of said communication relay units are utilized, and all but one of said possible values of y are assigned;

(iv) in a final step, said (k+1)th T/R device, where k is the last possible value of y to be assigned, communicates with said first T/R device;

thereby to cause said first T/R device and said second T/R device to communicate through a plurality of communication relay units.

3. The apparatus defined in claim 2, wherein at least one of said plurality of communication relay units is not utilized for the communication between said first T/R device and said second T/R device.

4. The apparatus defined in claim 1, wherein said relay unit further comprises a telecommunication control unit coupled to each of said third T/R device and said fourth T/R device for selecting a mode of communication between said second T/R device and said third T/R device.

5. The apparatus defined in claim 4, wherein the mode of communication includes a mode selected from the group consisting of an Internet, a public telephone network and a private communications network.

6. The system defined in claim 1, wherein said relay unit includes a second input device, responsive to a person at a site of the relay unit, coupled to said fourth T/R device and operative to communicate with said first T/R device, for producing a treatment device control signal, thereby allowing control of the IMD by said on-site person.

7. The system defined in claim 1, wherein said relay unit comprises a third input device, responsive to a person at the site of the relay unit, coupled to said third T/R device and operative to communicate with said second T/R device, thereby allowing notification of said medical expert by said on-site person.

8. The apparatus defined in claim 1, wherein said second T/R device and said third T/R device are each connected to a public telephone network.

9. The apparatus defined in claim 1, wherein said first T/R device and said fourth T/R device include means for wireless duplex transmission between them.

10. The apparatus defined in claim 1, wherein said first T/R device and said second T/R device include means for duplex communication between them through a route which includes at least one of (1) transmission through said relay unit, and (2) transmission not through said relay unit.

11. The apparatus defined in claim 10, wherein said first and said second T/R device are operative to communicate through a plurality of separate routes.

12. The apparatus defined in claim 11, wherein at least one of said first T/R device and said second T/R device further comprise means for automatically selecting one of said routes of communication.

13. The apparatus defined in claim 11, wherein said second T/R device is responsive to said medical expert, for selecting the route of communication between said first and said second T/R device.

14. The apparatus defined in claim 11, wherein said routes include both a wired network and a wireless network.

15. A system of electronic medical apparatus for treating a human patient comprising at least one implantable medical device (IMD) adapted to be implanted in said patient, which may be alternatively automatically self-controlled and remotely controlled by a medical expert, said apparatus comprising, in combination:

(1) at least one IMD comprising, in combination:

(a) a first transmitting/receiving (T/R) device for transmitting medical data sensed from said patient to, and for receiving at least one remote control signal from, a remote station;

(b) an electronic medical treatment device for treating said patient in response to control signals applied thereto;
(c) a sensor circuit, having a sensor circuit output, for producing at least one sensor circuit output signal at said sensor circuit output in response to the medical data sensed from the patient; and
(d) a logic device coupled to each of
    (i) said sensor circuit output,
    (ii) said first T/R device, and
    (iii) said treatment device,
for
    (i) analysis of said at least one sensor circuit output signal,
    (ii) generating a remote station notification signal,
    (iii) generating at least one local treatment device control signal, and
    (iv) generating at least one remote treatment device control signal, in response to said received remote control signal;
wherein:
    said logic device analyzes said at least one sensor circuit output signal to detect a medical abnormality which requires notification of the medical expert at the remote location, and is operative to generate a notification signal, for consideration by said medical expert when said analysis reveals said medical abnormality;
    upon receipt of said notification signal, said first T/R device transmits said notification signal representing at least one medical state of said patient to the remote station;
    said logic device analyzes said at least one sensor circuit output signal to detect a medical abnormality which requires treatment and is operative to generate at least one local treatment device control signal, if required;
    said logic device is operative to generate at least one remote treatment device control signal in response to said at least one remote control signal received from the remote station by said first T/R device;
    said logic device determines whether to issue a notification signal, to issue a local treatment signal, to issue both a notification and a local treatment signal, or to issue neither a notification nor a local treatment signal, based on said analysis; and
(2) a remote station comprising, in combination:
    (a) a display device for displaying medical information from said patient for evaluation by said medical expert at the remote station, in response to the receipt of said notification signal transmitted from said at least one IMD;
    (b) a first input device, responsive to said medical expert, for producing at least one remote control signal for controlling said IMD; and
    (c) a second T/R device, coupled to said display device and said input device, for receiving said notification signal and for transmitting said at least one remote control signal;
wherein:
    said notification signal is transmitted from said first T/R device of said IMD to said second T/R device of said remote station; and
    said medical expert observes and analyzes said information representing at least one medical state of said patient via said display device, following receipt of said notification signal, based on said analysis, said medical expert may cause said input device to generate said at least one remote control signal; and
    said at least one remote control signal is transmitted from said second T/R device of said remote station via said first T/R device to the logic device of said IMD;
and wherein
    upon the expiration of a power down time interval following the latter of:
        (i) the transmission of said notification signal to said remote station, and
        (ii) the last received remote control signal,
    said logic device powers down said first T/R device until the occurrence of a further medical abnormality which requires notification;
whereby
    said IMD delivers therapy, if required, in response to one of said at least one local treatment device control signal and said at least one remote treatment device control signal; and
    said IMD limits its power requirement.

16. A system of electronic medical apparatus for treating a human patient comprising at least one implantable medical device (IMD) adapted to be implanted in said patient, which may be alternatively automatically self-controlled and remotely controlled by a medical expert, said apparatus comprising, in combination:
(1) at least one IMD comprising, in combination:
    (a) a first transmitting/receiving (T/R) device for transmitting medical data sensed from said patient to, and for receiving at least one remote control signal from, a remote station;
    (b) an electronic medical treatment device for treating said patient in response to control signals applied thereto;
    (c) a sensor circuit, having a sensor circuit output, for producing at least one sensor circuit output signal at said sensor circuit output in response to the medical data sensed from the patient; and
    (d) a logic device coupled to each of
        (i) said sensor circuit output,
        (ii) said first T/R device, and
        (iii) said treatment device,
    for
        (i) analysis of said at least one sensor circuit output signal,
        (ii) generating a remote station notification signal;
        (iii) generating at least one local treatment device control signal, and
        (iv) generating at least one remote treatment device control signal, in response to said received remote control signal;
    wherein:
        said logic device analyzes said at least one sensor circuit output signal to detect a medical abnormality which requires notification of the medical expert at the remote location, and is operative to generate a notification signal, for consideration by said medical expert when said analysis reveals said medical abnormality;
        upon receipt of said notification signal, said first T/R device transmits said notification signal representing at least one medical state of said patient to the remote station;
        said logic device analyzes said at least one sensor circuit output signal to detect a medical abnormality which requires treatment and is operative to generate at least one local treatment device control signal, if required;

said logic device is operative to generate at least one remote treatment device control signal in response to said at least one remote control signal received from the remote station by said first T/R device;

said logic device determines whether to issue a notification signal, to issue a local treatment signal, to issue both a notification and a local treatment signal, or to issue neither a notification nor a local treatment signal, based on said analysis; and (2) a remote station comprising, in combination:
  (a) a display device for displaying medical information from said patient for evaluation by said medical expert at the remote station, in response to the receipt of said notification signal transmitted from said at least one IMD;
  (b) a first input device, responsive to said medical expert, for producing at least one remote control signal for controlling said IMD;
  (c) a second T/R device, coupled to said display device and said input device, for receiving said notification signal and for transmitting said at least one remote control signal; and
  (d) a remote station handshake device, coupled to said second T/R device, for generating at least one remote station handshake signal;

wherein:
  said notification signal is transmitted from said first T/R device of said IMD to said second T/R device of said remote station; and
  said medical expert observes and analyzes said information representing at least one medical state of said patient via said display device, following receipt of said notification signal,
  based on said analysis, said medical expert may cause said input device to generate said at least one remote control signal; and
  said at least one remote control signal is transmitted from said second T/R device of said remote station via said first T/R device to the logic device of said IMD;

and wherein:
  (I) receipt of said notification signal by said remote station causes said remote station handshake device to generate a remote station handshake signal for transmission by said second T/R device to said first T/R device;
  (II) receipt of said remote station handshake signal by said IMD causes said IMD logic device to generate an IMD handshake signal for transmission by said first T/R device to said second T/R device;
  (III) receipt of said IMD handshake signal by said remote station causes said remote station handshake device to generate another remote station handshake signal for transmission to said IMD; and
  (IV) said steps (II) and (III) continue to repeat sequentially;

whereby
  said IMD delivers therapy, if required, in response to one of said at least one local treatment device control signal and said at least one remote treatment device control signal; and
  each of said IMD logic device and said remote station handshake device, determine
  a presence of proper communication by the continuing timely receipt of respective handshake signals, and
  an absence of proper communication by an absence of timely receipt of respective handshake signals.

17. The apparatus defined in claim 16, wherein
(1) in a first operating mode said IMD logic device generates at least one local treatment device control signal based on analysis of said at least one sensor circuit output signal;
(2) in a second operating mode, said IMD logic device generates at least one remote treatment device control signal in response to at least one remote control signal received from the remote location by said first T/R device; and
(3) said IMD logic device selects said operating mode based on at least one signal received from at least one of said first T/R device and said sensor circuit.

18. The apparatus defined in claim 17, wherein
(a) a remote station handshake signal must be received by said IMD within a first time interval following the transmission of said notification signal, in order for an IMD handshake signal to be transmitted, and
(b) in the absence of a timely receipt by said IMD of said remote station handshake signal, said IMD is operative to cause at least one of:
  (i) generation of another notification signal;
  (ii) generation of a first communication failure signal for transmission to said remote station;
  (iii) changing the transmission mode of said first T/R device;
  (iv) changing the communication route between said first T/R device and said second T/R device;
  (v) increasing the power output of said first T/R device; and
  (vi) maintaining said first operating mode.

19. The apparatus defined in claim 17, wherein, following the transmission of a remote station handshake signal, in the absence of receipt of an IMD handshake signal by said remote station within a second time interval, said remote station is operative to cause at least one of:
  (i) generation of another remote station handshake signal;
  (ii) generation of a second communication failure signal for transmission to said IMD;
  (iii) changing the transmission mode of said second T/R device;
  (iv) increasing the power output of said second T/R device; and
  (v) changing the communication route between said second T/R device and said first T/R device.

20. The apparatus defined in claim 17, wherein, following the transmission of an IMD handshake signal, in the absence of receipt of a remote handshake signal by said IMD within a third time interval, said IMD is operative to cause at least one of:
  (i) generation of another IMD handshake signal;
  (ii) generation of a first communication failure signal for transmission to said remote station;
  (iii) changing the transmission mode of said first T/R device;
  (iv) changing the communication route between said first T/R device and said second T/R device;
  (v) increasing the power output of said first T/R device; and
  (vi) maintaining said first operating mode.

21. The apparatus defined in claim 19, wherein, upon receipt of said second communication failure signal, said IMD is operative to cause at least one of:
(i) generation of an IMD handshake signal;
(ii) changing the transmission mode of said first T/R device;
(iii) changing the communication route between said first T/R device and said second T/R device;
(iv) increasing the power output of said first T/R device; and
(v) maintaining said first operating state.

22. The apparatus defined in claim 18, wherein, upon receipt of said first communication failure signal, sail remote station is operative to cause at least one of:
(i) generation of a remote station handshake signal;
(ii) changing the transmission mode of said second T/R device;
(iii) increasing the power output of said second T/R device; and
(iv) changing the communication route between said second T/R device and said first T/R device.

23. The apparatus defined in claim 20, wherein, upon receipt of said first communication failure signal, said remote station is operative to cause at least one of:
(i) generation of a remote station handshake signal;
(ii) changing the transmission mode of said second T/R device;
(iii) increasing the power output of said second T/R device; and
(iv) changing the communication route between said second T/R device and said first T/R device.

24. The apparatus defined in claim 16, further comprising a communication relay unit including:
(1) a third transmitting/receiving (T/R) device for electronic communication with said second T/R device of said remote station; and
(2) a fourth transmitting/receiving (T/R) device, coupled to said third T/R device, for electronic communication with said first T/R device of said IMD;
wherein said IMD communicates with said remote station through said relay unit; and
wherein, in the absence of proper communication between said first T/R device and said second T/R device, at least one of:
a) said first T/R device and said fourth T/R device are operative to change communication modes;
b) said first T/R device and said fourth T/R device are operative to change communication routes;
c) said second T/R device and said third T/R device are operative to change communication modes;
d) said second T/R device and said third T/R device are operative to change communication routes;
e) said third T/R device is operative to increase transmitter power output; and
f) said fourth T/R device is operative to increase transmitter power output.

25. The apparatus defined in claim 18, further comprising a communication relay unit including:
(1) a third transmitting/receiving (T/R) device for electronic communication with said second T/R device of said remote station; and
(2) a fourth transmitting/receiving (T/R) device, coupled to said third T/R device, for electronic communication with said first T/R device of said IMD;
wherein said IMD communicates with said remote station through said relay unit; and
wherein, in the absence of a timely receipt by said IMD of said remote station handshake signal, said IMD is further operative to change at least one of:
a) the communication mode between said first T/R device and said fourth T/R device;
b) the communication route between said first T/R device and said fourth T/R device;
c) the communication mode between said second T/R device and said third T/R device;
d) the communication route between said second T/R device and said third T/R device;
e) the power output of said third T/R device; and
f) the power output of said fourth T/R device.

26. The apparatus defined in claim 19, further comprising a communication relay unit including:
(1) a third transmitting/receiving (T/R) device for electronic communication with said second T/R device of said remote station; and
(2) a fourth transmitting/receiving (T/R) device, coupled to said third T/R device, for electronic communication with said first T/R device of said IMD;
wherein said IMD communicates with said remote station through said relay unit; and
wherein, in the absence of a timely receipt by said remote station of said IMD handshake signal, said remote station is further operative to change at least one of:
a) the communication mode between said first T/R device and said fourth T/R device;
b) the communication route between said first T/R device and said fourth T/R device;
c) the communication mode between said second T/R device and said third T/R device;
d) the communication route between said second T/R device and said third T/R device;
e) the power output of said third T/R device; and
f) the power output of said fourth T/R device.

27. The apparatus defined in claim 20, further comprising a communication relay unit including:
(1) a third transmitting/receiving (T/R) device for electronic communication with said second T/R device of said remote station; and
(2) a fourth transmitting/receiving (T/R) device, coupled to said third T/R device, for electronic communication with said first T/R device of said IMD;
wherein said IMD communicates with said remote station through said relay unit; and
wherein, in the absence of a timely receipt by said IMD of said remote station handshake signal, said IMD is further operative to change at least one of:
a) the communication mode between said first T/R device and said fourth T/R device;
b) the communication route between said first T/R devices and said fourth T/R device;
c) the communication mode between said second T/R device and said third T/R device;
d) the communication route between said second T/R device and said third T/R device;
e) the power output of said third T/R device; and
f) the power output of said fourth T/R device.

28. The apparatus defined in claim 21, further comprising a communication relay unit including:
(1) a third transmitting/receiving (T/R) device for electronic communication with said second T/R device of said remote station; and (2) a fourth transmitting/receiving (T/R) device, coupled to said third T/R device, for electronic communication with said first T/R device of said IMD;

wherein said IMD communicates with said remote station through said relay unit; and wherein, upon receipt of said second communication failure signal, said IMD is further operative to change at least one of:
  a) the communication mode between said first T/R device and said fourth T/R device;
  b) the communication route between said first T/R device and said fourth T/R device;
  c) the communication mode between said second T/R device and said third T/R device;
  d) the communication route between said second T/R device and said third T/R device;
  e) the power output of said third T/R device; and
  f) the power output of said fourth T/R device.

29. The apparatus defined in claim 22, further comprising a communication relay unit including:
  (1) a third transmitting/receiving (T/R) device for electronic communication with said second T/R device of said remote station; and
  (2) a fourth transmitting/receiving (T/R) device, coupled to said third T/R device, for electronic communication with said first T/R device of said IMD;

wherein said IMD communicates with said remote station through said relay unit; and wherein, upon receipt of said first communication failure signal, said remote station is further operative to change at least one of:
    a) the communication mode between said first T/R device and said fourth T/R device;
    b) the communication route between said first T/R device and said fourth T/R device;
    c) the communication mode between said second T/R device and said third T/R device;
    d) the communication route between said second T/R device and said third T/R device;
    e) the power output of said third T/R device; and
    f) the power output of said fourth T/R device.

30. The apparatus defined in claim 23, further comprising a communication relay unit including:
  (1) a third transmitting/receiving (T/R) device for electronic communication with said second T/R device of said remote station; and
  (2) a fourth transmitting/receiving (T/R) device, coupled to said third T/R device, for electronic communication with said first T/R device of said IMD;

wherein said IMD communicates with said remote station through said relay unit; and wherein, upon receipt of said first communication failure signal, said remote station is further operative to change at least one of:
    a) the communication mode between said first T/R device and said fourth T/R device;
    b) the communication route between said first T/R device and said fourth T/R device;
    c) the communication mode between said second T/R device and said third T/R device;
    d) the communication route between said second T/R device and said third T/R device;
    e) the power output of said third T/R device; and
    f) the power output of said fourth T/R device.

* * * * *